United States Patent [19]
Klein et al.

[11] Patent Number: 5,807,861
[45] Date of Patent: Sep. 15, 1998

[54] AMINE SUBSTITUTED XANTHINYL COMPOUNDS

[75] Inventors: J. Peter Klein, Vashon; Gail E. Underiner, Brier; Anil M. Kumar, Seattle; Lance H. Ridgers, Bothell; Glenn C. Rice, Seattle; David W. Leung, Mercer Island, all of Wash.

[73] Assignee: Cell Therapeutics, Inc., Seattle, Wash.

[21] Appl. No.: 476,911

[22] Filed: Jun. 7, 1995

Related U.S. Application Data

[63] Continuation-in-part of Ser. No. 217,051, Mar. 24, 1994, abandoned.

[51] Int. Cl.⁶ ..................................................... A61K 31/52
[52] U.S. Cl. .............................................................. 514/263
[58] Field of Search ............................................... 514/263

[56] References Cited

U.S. PATENT DOCUMENTS

| | | | |
|---|---|---|---|
| 3,245,994 | 4/1966 | Klinger et al. | 544/272 |
| 3,422,107 | 1/1969 | Mohler et al. | 260/256 |
| 3,737,433 | 6/1973 | Mohler et al. | 260/256 |
| 4,061,753 | 12/1977 | Bodor et al. | 260/256 |
| 4,144,340 | 3/1979 | Offermans et al. | 544/273 |
| 4,275,064 | 6/1981 | Bodor et al. | 544/267 |
| 4,279,992 | 7/1981 | Boguslaski et al. | 435/7 |
| 4,299,832 | 11/1981 | Brown et al. | 544/267 |
| 4,374,837 | 2/1983 | Favier et al. | 544/271 |
| 4,515,795 | 5/1985 | Hinze et al. | 544/267 |
| 4,542,137 | 9/1985 | Klessing et al. | 514/265 |
| 4,558,051 | 12/1985 | Sunshine et al. | 514/261 |
| 4,565,817 | 1/1986 | Korbonits et al. | 514/263 |
| 4,576,947 | 3/1986 | Hinze et al. | 544/267 |
| 4,618,612 | 10/1986 | Baglioni | 514/265 |
| 4,636,507 | 1/1987 | Kreutzer et al. | 514/263 |
| 4,784,994 | 11/1988 | Romer et al. | 514/183 |
| 4,833,146 | 5/1989 | Gebert et al. | 544/267 |
| 4,845,081 | 7/1989 | Sloan | 514/258 |
| 4,965,271 | 10/1990 | Mandell et al. | 514/263 |
| 5,039,666 | 8/1991 | Novick, Jr. | 514/37 |
| 5,096,906 | 3/1992 | Mandell et al. | 514/263 |
| 5,118,500 | 6/1992 | Hänel et al. | 514/21 |
| 5,126,340 | 6/1992 | Tseng et al. | 514/233.2 |
| 5,196,439 | 3/1993 | Sugimoto et al. | 514/318 |
| 5,247,086 | 9/1993 | Cain et al. | 544/281 |
| 5,272,153 | 12/1993 | Mandell et al. | 514/263 |
| B1 3,737,433 | 3/1987 | Mohler et al. | 544/271 |

FOREIGN PATENT DOCUMENTS 9317684  9/1993  WIPO.

OTHER PUBLICATIONS

Bianco et al., *Blood*, 76: Supplement 1 (522), p. 133a, "Pentoxifylline (PTX) and GM–CSF Decrease Tumor Necrosis Factor–ALPHA (TNF–α) Levels in Patients Undergoing Allogeneic Bone Marrow Transplantation (BMT)", 1990.

Bianco et al., *Blood*, 78:5, pp. 1205–1211, "Phase I–II Trial of Pentoxifylline for the Prevention of Transplant–Related Toxicities Following Bone Marrow Transplantation", Sep. 1991.

Bursten et al., *The Journal of Biological Chemistry*, vol. 266, No. 31, pp. 20732–20743, "Interleukin–1 Rapidly Stimulates Lysophosphatidate Acyltransferase and Phosphatidate Phpsphohydrolase activities in Human Mesangial Cells", Nov. 1991.

Davis et al., *Applied Environment Microbial.*, 48:2, pp. 327–331, "Microbial Models of Mammalian Metabolism: Microbial Reduction and Oxidation of Pentoxifylline", Aug. 1984.

Ridder., *Chemical Abstracts*, vol. 60, col. 15892, "Derivatives of dialkylxanthines", Jan. 1964.

Singer et al., *Bone Marrow Transplantation*, 10:19, pp. 19–25, "Effect of Methylxanthine Derivatives on T Cell Activation", 1992.

*Primary Examiner*—Phyllis G. Spivack
*Attorney, Agent, or Firm*—McDermott, Will & Emery

[57] ABSTRACT

A method for treating a disease caused by an undesirable cell response mediated by a proliferative intracellular signaling pathway is provided wherein an effective amount of a compound is administered. The compound, resolved enantiomers, diastereomers, hydrates, salts, solvates and mixtures thereof, has the formula CORE MOIETY—$(R)_j$ wherein j is an integer from one to three; the core moiety is xanthinyl; and R is independently selected from the group consisting of amine, hydrogen, halogen, hydroxyl, $C_{(1-10)}$ alkyl, $C_{(2-10)}$ alkenyl, 2-bromopropyl, 4-chloropentyl, cyclohexyl, cyclopentyl, 3-dimethylaminobutyl, 2-hydroxyethyl, 5-hydroxyhexyl, 3-hydroxy-n-butyl, 3-hydroxypropyl, 2-methoxyethyl, 4-methoxy-n-butyl, phenyl, and formula I, at least one R comprising formula I

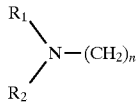

wherein $(CH_2)_n$ is optionally substituted; n is an integer from five to twenty; each $R_1$ or $R_2$ is independently hydrogen or an optionally substituted group that is herein defined; and wherein, when the $(CH_2)_n$, $R_1$ or $R_2$ is substituted, a substituent is selected from the group consisting of carbamoyl, primary, secondary and tertiary amino, $C_{(2-8)}$ alkenyl, $C_{(1-8)}$ alkyl, $C_{(1-8)}$ alkoxyl, $C_{(1-8)}$ hydroxyalkyl, azido, carbonato, carbonyl, carboxyl, cyano, $C_{(1-8)}$ haloalkyl, isocyano, isomercaptocyano, phospho, phosphonato, sulfonato, alkylsulfonyl, alkylsulfoxidyl, mercaptocarbonyl, mercaptocarbonato, thioureido and ureido.

21 Claims, 23 Drawing Sheets

AMINE SUBSTITUTED XANTHINYL COMPOUNDS

CROSS REFERENCE TO RELATED APPLICATIONS

This is a Continuation in Part of U.S. application Ser. No. 08/217,051, filed Mar. 24, 1994, abandoned.

TECHNICAL FIELD OF THE INVENTION

The invention provides for a class of amine-substituted compounds that are effective agents for inhibiting specific cellular signaling events often induced by noxious or inflammatory stimuli, or to be anti-microbial to yeast or fungal infections, directly or indirectly (i.e., immune stimulation). More specifically, the inventive compounds have at least one amine-containing substituent bonded to a core moiety. The inventive compounds are useful antagonists for controlling intracellular levels of specific non-arachidonyl sn-2 unsaturated phosphatidic acids and corresponding phosphatidic acid-derived diacylglycerols, which occur in response to cellular proliferative stimuli. In addition, the compounds are useful in treating or preventing, for example, sepsis syndrome, hematopoietic or organ toxicity, cancer, viral activity, AIDS and AIDS-related indications, allopecia caused by cytotoxic therapies, and progression of an inflammatory or autoimmune disease.

BACKGROUND OF THE INVENTION

Pentoxifylline [1-(5-oxohexyl)-3,7-dimethylxanthine], abbreviated PTX, is a xanthine derivative widely used medically for increasing blood flow. U.S. Pat. Nos. 3,422,107 and 3,737,433, both to Mohler et al. disclose PTX. Metabolites of PTX were summarized in Davis et al., "Microbial Models of Mammalian Metabolism: Microbial Reduction and oxidation of Pentoxifylline," *Applied and Environmental Microbiology*, Vol. 48, No. 2, pages 327–381, August 1984, and Bryce et al., "Metabolism and Pharmacokinetics of $^{14}$C-Pentoxifylline in Healthy Volunteers,"*Arzneim.-Forsch./Drug Res.* Vol. 39, No. 4, pages 512–517, 1989. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947 to Hinze et al. Other metabolites include 1-(5-pentyl)-3,7-dimethylxanthine carboxylic acid, designated M4, and 1-(4-butyl)-3,7-dimethylxanthine carboxylic acid, designated M5. In addition, U.S. Pat. Nos. 4,833,146 and 5,039,666 to Gebert et al. and Novick, respectively, disclose use of tertiary alcohol analogs of xanthine for enhancing cerebral blood flow.

PTX and its known metabolites thereof have been shown to have in vivo activity in specific biologic systems. U.S. Pat. No. 4,636,507 to Kreutzer et al. describes an ability of PTX and M1 to enhance chemotaxis in polymorphonuclear leukocytes responding to chemotaxis stimulation. In addition, PTX and related tertiary alcohol substituted xanthines inhibit activity of certain cytokines to affect chemotaxis as described in U.S. Pat. Nos. 4,965,271 and 5,096,906 to Mandell et al. Furthermore, by co-administrating PTX and GM-CSF, patients undergoing allogeneic bone marrow transplant exhibited decreased levels of tumor necrosis factor, TNF. Bianco et al., "Pentoxifylline (PTX) and GM-CSF Decrease Tumor Necrosis Factor (TNF-α) Levels in patients undergoing allogeneic Bone Marrow Transplantation (MBT)," *Blood*, Vol. 76, No. 1, Suppl. 1 (522), page 133a, 1990. Reduction in assayable levels of TNF was accompanied by reduced BMT-related complications. However, in normal volunteers, TNF levels were higher among PTX recipients. Therefore, elevated levels of TNF are not the primary cause of such complications.

Further research with PTX, its metabolites and their activity relating to various biologic systems spurred investigations with potential therapeutic agents heretofore unknown. These agents were identified as potential therapies for treating or preventing disease by inhibiting secondary cellular response to an external or in situ primary stimuli. These investigations sought efficacious therapeutic compounds which would be safe and effective for human or animal administration and would maintain cellular homeostasis in the presence of a variety of inflammatory stimuli.

Many diseases are difficult to treat because they have complex mechanisms of action, and multiple, adverse effects on a subject. As an example, cancer has been difficult to treat for this and other reasons. Precise causes of cancer remain unknown. Malignant tumor growth results from many physiologic factors. Cancer cells metastasize (i.e., break through blood vessels and travel to distant body sites) and secrete enzymes called metalloproteases, which "break down" blood vessel walls, allowing the cancer cells to enter the bloodstream and form remote tumors (proteolysis). In addition, tumor cell adhesion receptors (integrins) effect attachment—necessary for tumor residence in organs—of tumor cells to blood vessel walls and normal organs. Cancer cells also secrete certain proteins, such as BFGF, that stimulate new blood vessel development (angiogenesis), these new blood vessels supplying nutrients to promote malignant tumor growth.

Conventional antineoplastic therapies, such as, for example, antimetabolites, alkylating agents and antitumor agents (which target or interfere with DNA and/or synthesis of DNA or its precursors), and biologic therapies (including selective interferons, interleukins and other factors) have significant adverse side effects in patients, not limited to acute toxicity due to effects on rapid-proliferating tissues, such as bone marrow and oral epithelium, myelosuppression and mucositis, renal failure and neurological, hepatic or pulmonary toxicity. Thus, for example, a cancer therapy which effectively prevented, reduced or eliminated malignant tumors without causing deleterious side effects would provide previously unknown treatment.

Searching for potential disease treatments which would prevent or treat a disease with minimal or no adverse side effects, compounds were discovered having biologic activity in multifarious, predictive assays, indicating potential therapy in treating a broad spectrum of clinical indications acting via a variety of disease mechanisms. However, all these mechanisms appear to affect the second messenger pathway. Results of this research are the subject matter of this disclosure, the compounds discussed herein having structures and remarkable and surprising properties heretofore unknown.

SUMMARY OF THE INVENTION

The invention provides amine-substituted compounds and pharmaceutical compositions and uses thereof. The inventive amine-substituted compounds are useful in a large variety of therapeutic indications for treating or preventing disease. In particular, the inventive compounds and pharmaceutical compositions thereof provide therapy for diseases caused or advanced by intracellular signaling through specific intracellular signaling pathways, specifically the pathways discussed herein, by inhibiting a proliferative signaling pathway. Abnormally-induced intracellular signaling is characteristic of diseases treatable using the inventive compounds.

The inventive compounds have the formula:

CORE MOIETY—(R)$_j$ including resolved enantiomers and/or diastereomers, hydrates, salts, solvates or mixtures thereof. In this formula, j is an integer from one to three, the core moiety is non-cyclic or cyclic and R may be an amine, hydrogen, halogen (preferably bromine, chlorine, fluorine and iodine), hydroxyl, substituted or unsubstituted $C_{(1-10)}$ alkyl, $C_{(2-10)}$ alkenyl, a carbocyclic or heterocyclic group or formula I:

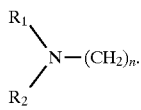

The inventive compounds have at least one R of formula I. In formula I, n is an integer from four to twenty, preferably 5 to sixteen, more preferably seven to fourteen; each $R_1$ or $R_2$ is independently hydrogen, substituted or unsubstituted $C_{(1-20)}$ alkyl, $C_{(1-20)}$ alkoxyl, $C_{(2-20)}$ alkenyl or carbocyclic or heterocyclic group, the alkyl or alkenyl being preferably substituted by an aryl, halogen or ketone group. Preferably, n is an integer from four to fourteen and more preferably n is an integer from six to ten. Optionally, $(CH_2)_n$ may 1) be substituted by a substituted or unsubstituted $C_{(1-10)}$ alkyl or $C_{(2-10)}$ alkenyl group; or 2) have one or two unsaturated bonds (preferably in a cis configuration). In most preferred compounds of the invention, $R_1$ and $R_2$ are both hydrogen or methyl or one of $R_1$ or $R_2$ is hydrogen and the other of $R_1$ or $R_2$ is an unsubstituted $C_{(1-20)}$ alkyl or a $C_{(1-20)}$ alkyl substituted by an unsubstituted heterocycle.

The inventive compounds are active therapeutic agents by virtue of an ability to prevent a second messenger signal from effecting an undesirable cell response. The core moiety serves as an orienting or plasma membrane-anchoring moiety. The orienting moiety may spacially orient the (R) structural component(s) of the inventive compounds, having the appropriately-substituted amine functional group, to an active site of an enzyme involved in phospholipid-based second messenger cellular signaling. Therefore, a large number of core moieties are active by virtue of their ability to orient a compound in a cellular plasma membrane.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol, thioester or the like. Exemplary core moiety amino acids may include, but are not limited to, one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be an amide, carboxyl ester, carboxide, hydrogen, hydroxide or a dipeptide comprising two amino acids selected from the foregoing exemplary list. A non-cyclic, halogen-core moiety may be, for example, bromine, chlorine, fluorine or iodine.

A cyclic core may be at least one five- to seven-member, non-heterocyclic (i.e., carbocyclic) ring or a heterocycle. The at least one five- to seven-membered cyclic core may preferably have from one to three, five- to six-membered ring structures in a predominantly planar configuration. An exemplary, non-heterocyclic ring core moiety may be selected from the group consisting of substituted or unsubstituted benzene; biphenyl; cyclohexane; cyclohexanedione; cyclopentanedione; napthlalene; phenol; quinone; salicylic acid; stilbene and tricyclododecane.

Although other heterocyclic cores are within the scope of the invention, the following representative cores are preferred: substituted or unsubstituted barbituric acid; benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; purine; pyridine; pyrimidine; pyrrole amide; quaternized N-heterocyclic; quinolizinedione; quinazolinone; quinoline; resorcinol; succinimide; theobromine; thymine; triazine; uric acid; uracil; vitamins A, E or K; or xanthine.

Preferably, R is bonded to a nitrogen of the core moiety, if present, most preferably to the nitrogen of a glutarimide, methylthymine, thymine, uracil or xanthine core. In representative, preferred compounds, R of formula I may be bonded to an $N_1$ nitrogen of glutarimide; $N_1$ nitrogen of xanthine (and $N_3$ and $N_7$ xanthine nitrogens may be independently substituted by a member selected from the group consisting of hydrogen, $C_{(1-6)}$ alkyl, fluoro, chloro and amino); $N_3$ nitrogen of methylthymine; or $N_1$ nitrogen of uracil. Alternatively, R having formula I may be bonded to $N_1$ and $N_3$ xanthine nitrogens and the $N_7$ xanthine nitrogen is substituted by a member selected from the group consisting of hydrogen, methyl, fluoro, chloro and amino.

The invention also provides a pharmaceutical composition. Pharmaceutical compositions of the inventive compounds comprise a pharmaceutical carrier or diluent and an effective amount of an inventive compound. Of course, the nature of the composition and the pharmaceutical carrier or diluent will depend upon the intended route of administration, for example, parenterally, topically, orally or by inhalation.

The invention includes a method for treating an individual having a variety of diseases. The disease is characterized by or can be treated by inhibiting an immune or cellular response to external or in situ primary stimuli. The disease states are mediated by a cellular response wherein intracellular signaling is mediated through a specific phospholipid-based second messenger pathway functioning within the cell and whose enzymes are located primarily, although not exclusively, near an inner leaflet of a cell plasma membrane. Various noxious or proliferative stimuli activate the second messenger pathway. Moreover, specific cytokines signal through specific phosphatidic acid intermediates, differentiated by the nature of fatty acids. This activation of the second messenger pathway is characteristic of disease states treatable using the inventive compounds or pharmaceutical compositions thereof. A biochemistry of this second messenger pathway is described herein. Thus, more specifically, the invention provides methods for treating or preventing clinical symptoms of various disease states or reducing toxicity of other treatments by inhibiting cellular signaling through a second messenger pathway involving signaling through phosphatidic acid.

A disease state or treatment-induced toxicity, treatable with an inventive compound or pharmaceutical composition thereof, include, but are not limited to, for example: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by T cell or B cell immune system dysregulation (treatable by suppression of the T cell or B cell responses); acute allergic reactions including, but not limited to, asthma and chronic inflammatory diseases—mediated by proinflammatory cytokines including (TNF) and interleukin-1 (IL-1)—and rheumatoid arthritis, osteoarthritis, multiple sclerosis or insulin-dependent diabetes mellitus (IDDM)—associated with enhanced localization of inflammatory cells and release of inflammatory cytokines and metalloproteases; smooth muscle cell, endothelial cell, fibroblast and other cell-type proliferation in response to growth factors, such as PDGF, FGF, endothelial growth factor (EGF), etc. (i.e., atherosclerosis, restenosis, stroke, and coronary artery disease); activation of human immunodeficiency virus infection (AIDS and AIDS related complex); HIV-associated dementia; kidney mesangial cell proliferation in response to IL-1, MIP-1α, PDGF or FGF; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); inflammation, particularly when in response to inflammatory stimuli (e.g., TNF, IL-1 and the like) or characterized by production of metalloproteases or allergies due to degranulation of mast cells and basophils in response to IgE or RANTES; bone diseases caused by overproduction of osteoclast-activating factor (OAF) by osteoclasts; central nervous system disorders (CNS) diseases resulting from over-stimulation by proinflammatory neurotransmitters such as; acetylcholine, serotonin, leuenkephalin or glutamate; acute inflammatory diseases such as septic shock and adult respiratory distress syndrome; multi-organ dysfunction associated with inflammatory cytokine cascade; and combinations thereof.

DETAILED DESCRIPTION OF THE INVENTION

Figure 1:
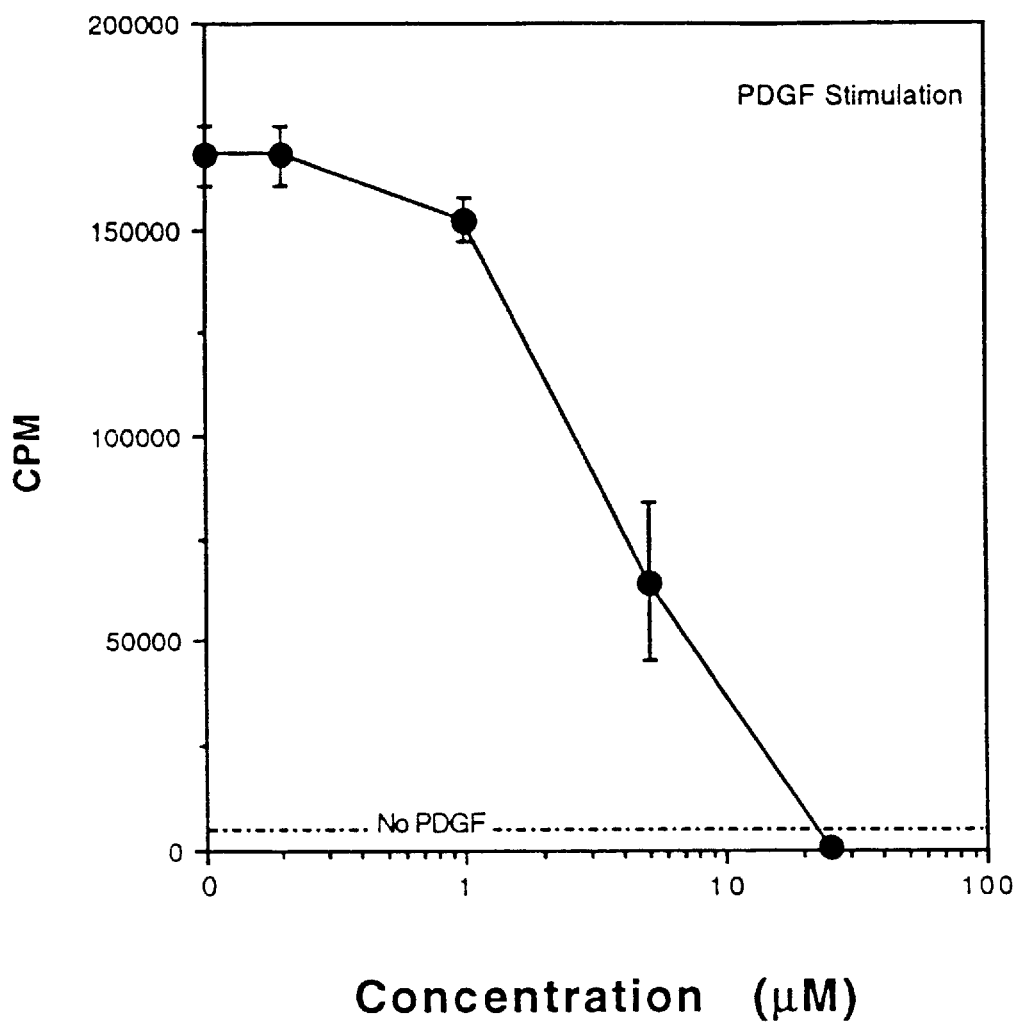
FIG. 1 shows an effect of inventive compound no. 3506 on proliferation of human stromal cells stimulated by PDGF.

The inventive compounds may control cell behavior by a particular phase of a second messenger pathway system (Bursten et al., "Interleukin-1 Rapidly Stimulates Lysophosphatidate Acyltransferase and Phosphatidate Phosphohydrolase Activities in Human Mesangial Cells," *J. Biol. Chem.*, Vol. 266, No. 31, pages 20732–20743, Nov. 5, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA$_2$=phospholipase A$_2$
PLD=phospholipase D
PAA=phosphoarachidonic acid
PC=phosphatidyl choline "remodeled" PA, cyclic pathway=PAA, LPA, PA and DAG intermediates substituted with 1-saturated, 2-linoleoyl or 1,2-dioleoyl, dioleoyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. The inventive compounds reduce or eliminate elevated PA and DAG.

These inventive compounds and pharmaceutical compositions are capable of, among other things, inhibiting subspecies of LPAAT and PAPH enzymes with substrate specificity for intermediates with 1,2-diunsaturated and 1-alkyl, 2-unsaturated subspecies. PTX also blocks PAPH in a specific activation pathway that does not involve PI but rather derives from a PA that is largely composed of 1,2-diunsaturated and 1-alkyl, 2-unsaturated subspecies. This was shown, for example, by the demonstration that TNF-stimulated human mesangial cells produce DAG from PI and regenerate PI with or without PTX present. In the latter system there is no evidence to suggest that PA or DAG are derived from sources other than PI. In contrast, the inventive compounds affect that subset of PAPH and LPAAT relating to substrates with unsaturated fatty acids other than arachidonate in the sn-2 position, not the housekeeping forms of these enzymes that serve the PI pathway.

The second messenger pathway of most significance in the invention involves substrates with unsaturated fatty acids in the sn-2 position other than arachidonate and those sub-species of PAPH and LPAAT and are not involved in normal cellular housekeeping functions, which are part of a classical PI pathway. The PAPH and LPAAT enzymes involved in this specific second messenger pathway are stereo-specific for different acyl side chains and substrate isomers. Therefore, the inventive compounds may preferably be substantially enantiomerically pure.

IL-1 activates (through the Type I IL-1 receptor) a lyso-PA acyltransferase (LPAAT) and phosphatidate phosphohydrolase (PAPH) within 5 seconds of cell (for example, human mesangial cells, HMC) exposure. Activation of both enzymes results in production of PA species with sn-i and sn-2 unsaturated acyl groups, with the majority of sn-2 acyl chains being polyunsaturated. Both IL-1 and a product of LPAAT (1,2-sn-dilinoleoyl PA) activate a signaling pathway involving hydrolysis of PE to PA. This reaction is followed by dephosphorylation of PA to produce both 1,2-sn-diacylglycerol and 1-o-alkyl, or 1-o-alkenyl, acylglycerol (AAG) species. The inventive compounds exert their activity by inhibiting one or both enzymes at an inner leaflet of the plasma membrane. Therefore, appropriate in vitro models for drug activity may measure inhibition of stimulation caused by a proinflammatory cytokine or other inflammatory cellular signal.

Generation of sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is less than about 0.1% of total membrane lipid mass, is sufficient to activate PLD activity. This quantity of PA is similar to that endogenously synthesized by LPAAT. The PA-stimulated PLD acts upon PE, should localize to the inner leaflet of the cell membrane, enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 minutes) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG upon stimulation with mitogens, although the sources of DAG differ between experimental systems. In nontransformed renal mesangial cells, IL-1β stimulation increased PLA$_2$ and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. A particular specie of serum-stimulated DAG is dioleoyl and of PA are dilinoleoyl and dioleoyl. This upregulation occurs over 4–12 hours and pretreatment of cells with an inventive compound, blocks generation of these phospholipid second messengers. The inhibition occurs either through suppressing PA generation de novo from lysoPA, or through inhibition of one or both arms of the Lands cycle. A corresponding lysoPA increase with diminished PA/DAG production suggests inhibition of transacylation of a precursor lipid. Therefore, the ras transformation mediates an upregulation of PA through indirect stimulation of PLA$_2$ and/or LPAAT activity. The inventive compounds inhibit conversion of upregulated lysoPA to PA and subsequently block phenotypic changes induced by PA/DAG in the membrane.

Therapeutic Uses of the Inventive Compounds

Inhibition of second messenger pathway activation, as described above, predicts that the inventive compounds are useful in treating a wide variety of clinical indications mediated at the cellular level by a common mechanism. Moreover, in vitro data presented herein provides predictive evidence that a wide variety of clinical indications, having similar effects on the selective second messenger pathway, may be treated by the inventive compounds. These compounds specifically inhibit the second messenger signaling pathway described above. In fact, the mechanism of action of the inventive compounds explains why these compounds have multifarious applications in treating a broad variety of clinical indications.

Activation of the second-messenger pathway is a significant mediator of response to noxious stimuli and results in cellular signals that lead to, for example, acute and chronic inflammation, immune response and cancer cell growth. Although the inventive compounds may desirably inhibit other noxious stimuli not discussed, they most effectively mediate the above conditions. Signals mediated by the present second messenger pathway include, for example, those cellular responses of lipopolysaccharide (LPS) directly; T cell activation by antigen; B cell activation by antigen, cellular responses to IL-1 (mediated through the IL-1 Type I receptor but not the IL-1 Type II receptor) and TNF (Type I receptor), growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

Several compounds are particularly useful as inhibitors of IL-2-induced proliferative responses. Inhibiting IL-2 signaling is potentially useful in treating numerous diseases characterized by T-cell activation and hyperproliferation. Representative autoimmune diseases treated by inhibiting IL-2 signaling include, but are not limited to, lupus, scleroderma, rheumatoid arthritis, multiple sclerosis, glomerula nephritis as well as potential malignancies, such as, for example, chronic myelogenous leukemia as well as others.

The inventive compounds: (1) block IL-1 signal transduction through the Type 1 receptor as shown, for example, by preventing IL-1 and IL-1 plus PDGF-induced smooth muscle, endothelial and kidney mesangial cell proliferation;

(2) suppress up-regulation of adhesion molecules as shown, for example, by blocking VCAM in endothelial cells; (3) inhibit TNF-, LPS- and IL-1-induced metalloproteases (an inflammation model); (4) block LPS-, TNF- or IL-1-induced metalloprotease and secondary cytokine production (modeling prevention or treatment of septic shock); (5) suppress T cell and B cell activation by antigen, for example, IL-2 and IL-4; (6) inhibit mast cell activation by immunoglobulin E (IgE); (7) are cytotoxic for transformed cells and tumor cell lines, yet not for normal cells; and (8) block signaling by IL-2, IL-4, IL-6 and IL-7 on T and B cells.

The foregoing molecular and cellular effects give rise to the following therapeutic and pharmacologic effects, including, but not limited to: protection and treatment of endotoxic shock and sepsis induced by gram positive or gram negative bacteria; inhibition of tumor cell growth; synergistic immunosuppression active in autoimmune diseases and in suppressing allograft reactions; and stimulation of hair grow through reversal of an apoptotic process. The inventive compounds are most potent when used to prevent and/or treat septic shock, acute and chronic inflammatory disease, cancer growth and an autoimmune disease.

The inventive compounds also are useful as an adjuvant to inhibit toxic drug side effects (ie., Il-2, amphotericin B and cytoreductive therapies) mediated through the second messenger pathway. Furthermore, the compounds of the invention are able to decrease enhanced levels of a relevant PA and DAG resulting from stimulation of synaptosomes with acetylcholine and/or epinephrine. This predicts that the effects of the compounds of the invention are to both enhance the release of inhibitory neural transmitters such as dopamine, and to modulate the distal "slow current" effects of such neurotransmitters.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus BFGF, a 72 Kd type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 Kd type IV collagenase) involved in normal tissue remodeling.

The inventive compounds inhibit signal transduction mediated through the Type I IL-1 receptor, and are therefore considered as IL-1 antagonists. A review article described the role of IL-1 as "an important rapid and direct determinant of disease. In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." Dinarello et al., "The Role of Interleukin-1 in Disease," *N. Engl. J. Med.,* Vol. 328, page 106, Jan. 14, 1993. The article describes a group of diseases that are mediated by IL-1, including sepsis syndrome, rheumatoid arthritis, inflammatory bowel disease, acute and myelogenous leukemia, IDDM, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above- mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure and doses of 300 ng or more per kilogram of body weight may cause severe hypotension. The therapeutic advantage of blocking the action of IL-1 resides in preventing its deleterious biological effects without interfering with the production of molecules that have a role in homeostasis. The present inventive compounds address this need, identified by Dinarello et al., by inhibiting cellular signaling only through the IL-1 Type I receptor and not through the IL-1 Type II receptor.

With regard to rheumatoid arthritis, Dinarello et al. state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$), leukotriene $B_4$ ($LTB_4$) and IL-8, an inflammatory cytokine with neutrophil-chemoattractant and neutrophil-stimulating properties. Tissue concentrations of $PGE_2$ and $LTB_4$ correlate to severity of disease in patients with ulcerative colitis. Patients with inflammatory bowel disease have high tissue concentrations of IL-1 and IL-8. Therefore, an IL-1 antagonist, such as the inventive compounds, are effective to treat inflammatory bowel disease.

With regard to acute and chronic myelogenous leukemia, there is increasing evidence that IL-1 acts as a growth factor for such tumor cells. Therefore, the inventive compounds are effective to prevent the growth of worsening of disease for acute and chronic myelogenous leukemias.

IDDM is considered to be an autoimmune disease destroying beta cells in the islets of Langerhans, mediated by immunocompetent cells. Islets of animals with spontaneously occurring IDDM (e.g., BB rats or NOD mice) have inflammatory cells that contain IL-1. Therefore, the inventive compounds are useful for preventing and treating IDDM.

IL-1 also plays a role in atherosclerosis development. Endothelial cells are a target of IL-1. IL-1 stimulates proliferation of vascular smooth muscle cells. Foam cells, isolated from fatty arterial plaques from hypercholesterolemic rabbits, contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds are useful in preventing and treating atherosclerosis.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the selective second messenger cellular phospholipid-based signaling pathway and by excessive or unregulated production of "first messenger" inflammatory cytokines such as TNF or IL-1. With regard to TNF primary stimuli, there are several disease states in which excessive or unregulated TNF production by monocytes/macrophages is implicated in exacerbating or causing the disease. These include, but are not limited to, for example, neurodegenerative diseases such as Alzheimer's disease, endotoxemia or toxic shock syndrome (Tracey et al., "Anti-cachectin/TNF Monoclonal Antibodies Prevent Septic Shock During Lethal Bacteraemia," *Nature,* Vol. 330, pages 662–664, 1987 and Hinshaw et al., "Survival of Primates in LD$_{100}$ Septic Shock Following Therapy With Antibody to Tumor Necrosis Factor (TNFα)," *Circ. Shock,* Vol. 30, pages 279–292, 1990); cachexia (Dezube et al., "Pentoxifylline and Wellbeing in Patients with Cancer," *The Lancet,* page 662, 1990), and adult respiratory distress syndrome (Millar et al., "Tumour Necrosis Factor in Bronchopulmonary Secretions of Patients with Adult Respiratory Distress Syndrome," *The Lancet,* Vol. 1, pages 712–713, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., "Tumor Necrosis Factor and Disease Severity in Children with Falciparum Malaria," *N. Engl. J. Med.,* Vol. 320, No. 24, pages 1586–1591, 1989), chronic pulmonary inflammatory diseases such as silicosis and asbestosis (Piguet et al., "Requirement of Tumour Necrosis Factor for Development of Silica-induced Pulmonary Fibrosis," *Nature,* Vol. 344, pages 245–247, 1990, and Bissonnette et al., "Pulmonary Inflammation and Fibrosis in a Murine Model of Asbestosis and Silicosis," *Inflammation,* Vol. 13, No. 3, pages 329–339, 1989), and reperfusion injury (Vedder et al., "Inhibition of Leukocyte Adherence by Anti-CD18 Monoclonal Antibody Attenuates Reperfusion Injury in the Rabbit Ear," *Proc. Natl. Acad. Sci. USA,* Vol. 87, pages 2643–2646, 1990).

The inventive compounds provide a method for maintaining homeostasis in cells contacted by primary stimuli by mitigating the effects of these primary stimuli on the secondary signaling pathways invoked within seconds of a primary stimulus. For example, administration of an inventive compound in vivo or ex vivo provides a method to modify cellular behavior, the method comprising contacting cells (in vivo or ex vivo), whose behavior is to be modified, with an effective amount of an inventive compound or a pharmaceutical composition thereof wherein said method is a method to: (1) inhibit proliferation of tumor cells; (2) suppress activation of T-cells by antigen or IL-2 stimulation; (3) suppress activation of monocyte/macrophage cells by endotoxin, TNF, IL-1 or GM-CSF stimulation; (4) suppress antibody production of B-cells in response to an antigen, IL-4 or CD40 ligand; (5) inhibit proliferation of smooth muscle cells in response to growth factors capable of stimulating said proliferation; (6) lower systemic vascular resistance conferred by endothelial cells by reducing release of hypertension-inducing substances; (7) lower systemic vascular resistance induced by endothelial cells by enhancing release of anti-hypertensive substances; (8) lower expression of adhesion molecules induced by enhancers thereof; (9) suppress activation of T-cells and macrophages by HIV, thus inhibiting viral replication; (10) inhibit proliferation of kidney mesangial cells in response to stimulation by IL-1 and/or MIP-1α and/or PDGF and/or FGF; (11) enhance resistance of kidney glomerular or tubular cells to cyclosporin A or amphotericin B; (12) prevent release of MIP-1α by IL-1, TNF, or endotoxin stimulated monocytes and macrophages; (13) prevent release of platelet activating factor by IL-1, TNF, or endotoxin treated megakaryocytes, fibroblastic cells, and macrophages; (14) prevent downregulation of receptors for cytokines in TNF-treated hematopoietic progenitor cells; (15) suppress production of metalloproteases in IL-1- or TNF-stimulated glomerular epithelial or synovial cells; (16) enhance resistance of gastrointestinal or pulmonary epithelial cells to cytotoxic drugs or radiation; (17) enhance the antitumor effect of a non-alkylating antitumor agent; (18) to inhibit production of osteoclast activating factor in response to IL-1; (19) inhibit degranulation in response to IgE; (20) enhance release of adrenergic neural transmitters, dopamine, norepinephrine, or epinephrine, or the neurotransmitter, acetylcholine; (21) modulate postsynaptic "slow current" effects of adrenergic neurotransmitters, such as, dopamine, epinephrine, or norepinephrine, or the neurotransmitter acetylcholine; (22) suppress signaling by neurotransmitters including acetyl choline, leuenkephalin and serotonin; or (23) increase seizure threshold.

The compounds of the invention can inhibit certain VEGF, FGF, EGF and PDGF effects in vivo, such as inhibition of angiogenesis or restenosis. For example, Ferns et al. ("Inhibition of Neointimal Smooth Muscle Accumulation After Angioplasty by an Antibody to PDGF," *Science,* Vol. 253, pages 1129–1132, 1991) have shown that neointimal smooth muscle chemotaxis and angioplasty are inhibited in rats using a neutralizing antibody to PDGF. Also, Jawien et al. ("Platelet-derived Growth Factor Promotes Smooth Muscle Migration and Intimal Thickening in a Rat Model of Balloon Angioplasty," *J. Clin Invest,* Vol. 89, pages 507–511, 1992) have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., "Localization of PDGF-B Protein in Macrophages in All Phases of Atherogenesis," *Science*, Vol. 248, pages 1009–1012, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., "Expression of Messenger RNAs for Platelet-Derived Growth Factor and its Receptors in Human Sarcoma Cell Lines," *Int. J. Cancer*, Vol. 46, pages 1066–1070, 1990), metastatic melanoma cells (Yamanishi et al., "Differences in Basic Fibroblast Growth Factor RNA and Protein Levels in Human Primary Melanocytes and Metastatic Melanoma Cells," *Cancer Research*, Vol. 52, pages 5024–5029, 1992), and glial tumors (Fleming et al., "Amplification and/or Overexpression of Platelet-derived Growth Factor Receptors and Epidermal Growth Factor Receptor in Human Glial Tumors," *Cancer Research*, Vol. 52, pages 4550–4553, 1992).

The inventive compounds are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent toxicity to the central nervous system of dexamethasone or methylprednisolone, and to treat chronic pain without addiction to the drug. Further, the compounds of the invention are useful in the treatment of children with learning and attention deficits and may generally improve memory in subjects with organic deficits, including Alzheimer's patients.

Compounds of the Invention

The inventive compounds are useful therapeutic agents, inhibiting proinflammatory and neoplastic cellular signaling mechanisms and have the formula:

CORE MOIETY—(R)$_j$ including resolved enantiomers and/or diastereomers, hydrates, salts, solvates and mixtures thereof. In this formula, j is an integer from one to three, the core moiety is non-cyclic or cyclic and R may be an amine, hydrogen, halogen (preferably bromine, chlorine, fluorine and iodine), hydroxyl, substituted or unsubstituted $C_{(1-10)}$ alkyl, $C_{(2-10)}$ alkenyl, cyclic or heterocyclic group or formula I:

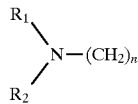

I

Preferred R substituents other than formula I include, but are not limited to, 2-bromopropyl, 4-chloropentyl, cyclohexyl, cyclopentyl, 3-dimethylaminobutyl, ethyl, hexyl, 2-hydroxyethyl, 5-hydroxyhexyl, 3-hydroxy-n-butyl, 3-hydroxypropyl, isobutyl, isopropyl, 2-methoxyethyl, 4-methoxy-n-butyl, methyl, n-butyl, n-propyl, phenyl, t-butyl and the like. Particularly preferred R having a structure other than formula I are ethyl, methyl, or hydrogen.

The inventive compounds have at least one R of formula I. In formula I, n is an integer from four to twenty; each $R_1$ or $R_2$ is independently hydrogen, substituted or unsubstituted $C_{(1-20)}$ alkyl, $C_{(1-20)}$ alkoxyl, $C_{(2-20)}$ alkenyl group, or cyclic or heterocyclic group, the alkyl or alkenyl being preferably substituted by an aryl, halogen or ketone group. Preferably, n is an integer from four to fourteen or and more preferably n is an integer from six to ten. Optionally, $(CH_2)_n$ may 1) be substituted by a substituted or unsubstituted $C_{(1-10)}$ alkyl or $C_{(2-10)}$ alkenyl group; or 2) have one or two unsaturated bonds (preferably in a cis configuration). In most preferred compounds of the invention, $R_1$ and $R_2$ are both hydrogen or methyl or one of $R_1$ or $R_2$ is hydrogen and the other of $R_1$ or $R_2$ is an unsubstituted $C_{(1-20)}$ alkyl or a $C_{(1-20)}$ alkyl substituted by an unsubstituted heterocycle.

Although other possible substituents are within the scope of the inventive compounds, when $R_1$ or $R_2$ is a substituted $C_{(1-20)}$ alkyl, $C_{(1-20)}$ alkoxyl, $C_{(2-20)}$alkenyl or cyclic or heterocyclic group, representative substituents may be selected from among amide, primary, secondary and tertiary amine, $C_{(2-8)}$ alkenyl, $C_{(1-8)}$ alkyl (including, e.g., branched and unbranched alkyl or alkenyl groups), $C_{(1-8)}$ alkoxyl, $C_{(1-8)}$hydroxyalkyl, azide, carbonate, carbonyl, carboxylic acid, cyanide, $C_{(1-8)}$ haloalkyl (including, e.g., mono-, di- and tri-haloalkyl substituents, such as trihalomethyl), isocyanate, isothiocyanate, phosphate, phosphonate, sulfonate, sulfone, sulfoxide, thioamide, thiocarbonate, thioester, thiolester, thiol, thiourea and urea.

When $(CH_2)_n$ is branched by a substituted $C_{(2-10)}$ alkyl or $C_{(2-10)}$ alkenyl group, corresponding substituents may also be selected from the foregoing list.

Representative $R_1$ or $R_2$ cyclic or heterocyclic groups include, but are not limited to: anthracene, bicyclo[4.4.0] decane, bicyclo[2.2.1]heptane, bicyclo[3.2.0]heptane, bicyclo[4.1.0]heptane, bicyclo[2.2.1]hexane, bicyclo[4.3.0] nonane, bicyclo[2.2.2]octane, biphenyl, cyclopentadiene, cyclopentane, cyclobutane, cyclobutene, cycloheptane, cyclohexane, cyclooctane and cyclopropane, 1,2-diphenylethane, fluorene, indene, phenyl, quinone, terphenyl, napthalene, phenanthrene, terphenyl, toluene, xylene, azetidine, benzofuran, benzothiophene, carbazole, furan, glutarimide, indole, isoquinoline, lactam, lactone, oxazole, oxetane, oxirane, phthalimide, piperidine, pyrrolidine, pyran, pyridine, pyrrole, quinoline, tetrahydrofuran, tetrahydropyran, tetrahydrothiophene, thiophene, thymine, derivatives thereof and the like. Due primarily to availability and ease of synthesis, more preferred cyclic groups include, but are not limited to, less complex ring systems, such as, for example, cyclopentane and cyclohexane, cyclopentadiene, phenyl, indene, toluene, xylene, furan, indole, thymine and xanthine.

The inventive compounds are active therapeutic agents by virtue of an ability to prevent a second messenger from effecting an undesirable cell response. The core moiety serves as an orienting or plasma membrane-anchoring moiety. The orienting moiety may spacially orient the (R) structural component(s) of the inventive compounds, having the appropriately-substituted amine functional group, to an active site of an enzyme involved in phospholipid-based second messenger cellular signaling. Therefore, a large number of core moieties are active by virtue of their ability to orient a compound in a cellular plasma membrane.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol, thiolester or the like. Exemplary core moiety amino acids may include, but are not limited to, one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be an amide, carboxyl ester, carboxide, hydrogen, hydroxide or a dipeptide comprising two amino acids selected from the foregoing exemplary list. A non-cyclic, halogen-core moiety may be, for example, bromine, chlorine, fluorine or iodine.

A cyclic core may be at least one five- to seven-member, non-heterocyclic (i.e., carbocyclic) ring or a heterocycle. The at least one five- to seven-membered cyclic core may preferably have from one to three, five- to six-membered ring structures in a predominantly planar configuration. An exemplary, non-heterocyclic ring core moiety may be selected from the group consisting of substituted or unsubstituted benzene; biphenyl; cyclohexane; cyclohexanedione; cyclopentanedione; napthlalene; phenol; quinone; salicylic acid; stilbene and tricyclododecane.

Although other heterocyclic cores are within the scope of the invention, the following representative cores are preferred: substituted or unsubstituted barbituric acid; benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; pyridine; pyrimidine; pyrrole amide; quaternized N-heterocyclic; quinolizinedione; quinazolinone; quinoline; resorcinol; succinimide; theobromine; thymine; triazine; uric acid; uracil; vitamins A, E or K; or xanthine.

Representative substituents for the non-heterocyclic or heterocyclic core moieties include, but are not limited to, for example, amide, primary, secondary and tertiary arnine, $C_{(2-8)}$ alkenyl, $C_{(1-8)}$ alkyl (including, e.g., branched and unbranched alkyl or alkenyl groups), $C_{(1-8)}$ alkoxyalkyl, azide, carbonate, carbonyl, carboxylic acid, cyanide, $C_{(1-8)}$ haloalkyl (including, e.g., mono-, di- and tri-haloalkyl substituents, such as trihalomethyl), isocyanate, isothiocyanate, phosphate, phosphonate, primary, secondary or tertiary alcohol (including, e.g., any one of various diols, methanol, butanol, 1-cyclopentanol, ethanol, 2-ethyl-3-methyl-1-propanol, pentanol, propanol, and methylcyclohexanol), sulfonate, sulfone, sulfoxide, thioamide, thiocarbonate, thioester, thiolester, thiol, thiourea and urea.

Preferred non-heterocyclic ring cores include, but are not limited to, substituted or unsubstituted 1,3-cyclohexanedione, 1,3-cyclopentanedione; 1,3-dihydroxynaphthalene; or orthophenol.

Preferred heterocyclic cores include, but are not limited to, substituted or unsubstituted 3,7-dimethylxanthine, glutarimide, methylthymine, methyluracil, 3-methylxanthine, thymine, uracil and xanthine, most preferably methyl-substituted xanthine. Exemplary preferred cores include, but are not limited to: $C_{(1-6)}$ alkyl-substituted thymine; $C_{(1-6)}$ alkyl-substituted uracil; 1,3-dihydroxynapthalene; 3,3-dimethylglutarimide; dihydrothymine; 2,4-dioxohexahydro-1,3,5-tetrazine; hexahydrophthalimide; homophthalimide; 2-hydroxypyridine; β-ionone as vitamin A methylbarbituric acid; 2,6,6-methyl-1-cyclohexene-1-acetaldehyde as vitamin A; methyldihydroxypyrazolopyrimidine, specifically, 1,3-dimethyldihydroxypyrazolo[4,3-d]pyrimidine; 1-methyl-5,6-dihydrouracil; 1,7-dimethylxanthine, 3,7-dimethylxanthine; 7-methylhypoxanthine; 1-methyllumazine; 3-methyl-7-methylpivaloylxanthine; methylpyrrolopyrimidine; 1-methylpyrrolo [2,3-d] pyrimidine; 1-methyl-2,4(1H,3H)-quinolizinedione (1-methylbenzoyleneurea); methylthymine; 1-methyluracil; 3-methylxanthine; orotic acid; prostacyclin; 1-pyrrole amides; 2-pyrrole amides; 3-pyrrole amides; quinazolin-4(3H)-one; 1,2,3,4-tetrahydroisoquinoline; tetrahydrophthalimide; sulindac; uracil fused to naphthalene; 5- and/or 6-position substituted uracils (such as, for example, 5-bromouracil); tetralone to vitamin K; and 8-substituted xanthines (having substituents such as N or S).

Preferably, R is bonded to a nitrogen of the core moiety, if present, most preferably to the nitrogen of a glutarimide, methylthymine, thymine, uracil or xanthine core. In representative, preferred compounds, R of formula I may be bonded to an $N_1$ nitrogen of glutarimide; $N_1$ nitrogen of xanthine (and $N_3$ and $N_7$ xanthine nitrogens may be independently substituted by a member selected from the group consisting of hydrogen, $C_{(1-6)}$ alkyl, fluoro, chloro and amino); $N_3$ nitrogen of methylthymine; or $N_1$ nitrogen of uracil. Alternatively, R having formula I may be bonded to $N_1$ and $N_3$ xanthine nitrogens and the $N_7$ xanthine nitrogen is substituted by a member selected from the group consisting of hydrogen, methyl, fluoro, chloro and amino.

Particularly preferred compounds of the invention are exemplified herein.

Synthesis of the Inventive Compounds

The invention is also directed to a method for preparing compounds according to the invention. The method is discussed in general below and in specific detail in the examples.

In the inventive method, a compound containing a desired core (intended as the "core moiety") undergoes a reaction to produce an anion, which is then subsequently reacted with a substituted ester, displacing a target functional group of the ester. A predetermined amount of the core-containing compound is reacted with a suitable base and the substituted ester in a solvent to form and ester product. The substituted ester has at least one functional group which may be substituted by the desired core-containing compound in the displacement reaction.

Preferred bases include, but are not limited to, sodium hydride, sodium amide, sodium alkoxide, lithium hydride, potassium hydride, lithium amide and potassium amide. An especially preferred base is sodium hydride. Preferred solvents may be dimethylsulfoxide, dimethylformamide, or an alcohol, such as, for example, methanol, ethanol or isopropanol. Any substituted ester comprising a chain structure of the final inventive compounds may be used. Preferred substituted esters include, but are not limited to halo-substituted esters.

The ester product, having a composite structure of the core-containing compound and substituted ester, may subsequently be converted by reacting it with an ester-hydrolyzing agent to obtain an intermediate carboxylic acid. Exemplary ester-hydrolyzing agents include, but are not limited to, potassium hydroxide or sodium hydroxide in water. The intermediate carboxylic acid is then reacted in a halogenation reaction with a halogenating agent to obtain a compound having a carboxylic acid halide functional group. Exemplary halogenating agents include, but are not limited to, thionyl chloride, phosphorus trichloride, phosphorus pentachloride, phosphorus oxychloride, thionyl bromide and the like. To obtain a substituted amide functional group, the compound having a carboxylic acid halide functional group is reacted with a substituted amine.

By then reacting the substituted amide with a suitable reducing agent, the substituted amide is reduced to the corresponding inventive amine-substituted compound. Exemplary reducing agents include, but are not limited to, borane-tetrahydrofuran complex and diisobutylaluminum-hydride.

Alternatively, a compound containing a desired core (intended as a "core moiety") undergoes a reaction to produce a halide product. A core-containing compound is reacted in a solvent with a suitable base and a substituted halide, the substituted halide having at least one other functional group which may be substituted in a displacement reaction by the desired core-containing compound.

In this reaction, preferred bases include, but are not limited to, sodium hydride, sodium amide, sodium alkoxide, lithium hydride, potassium hydride, lithium amide, sodium amide and potassium amide. An especially preferred base is sodium hydride. Preferred solvents may be dimethylsulfoxide, dimethylformamide, or an alcohol, such as, methanol, ethanol or isopropanol. Any substituted halide comprising a chain structure of the inventive compounds may be used in the preliminary reaction according to the invention. Preferred substituted halides may be halo-substituted halides (or dihalides).

The halide product, having a composite structure of the core-containing compound and substituted halide, may be converted to a corresponding compound having an azido group. The halide product is reacted with a salt of hydrazoic acid to obtain an azide. Hydrazoic acid salts may be selected from potassium azide, sodium azide, or lithium azide. Reducing the substituted azide using a suitable reducing agent results in an inventive compound. Reducing agents include, but are not limited to, hydrogen with palladium on carbon, hydrogen with Raney nickel, or hydrogen with platinum oxide.

Additionally, a substituted aldehyde or ketone, having a composite structure of the core-containing compound, and either a substituted aldehyde or a substituted ketone may be converted to an inventive compound in a reductive amination reaction using a substituted amine and suitable reducing agent. Exemplary reducing agents include, but are not limited to, sodium cyanoborohydride and sodium borohydride. Schematic representations of the inventive methods discussed above are illustrated in schematics A, B and C below:

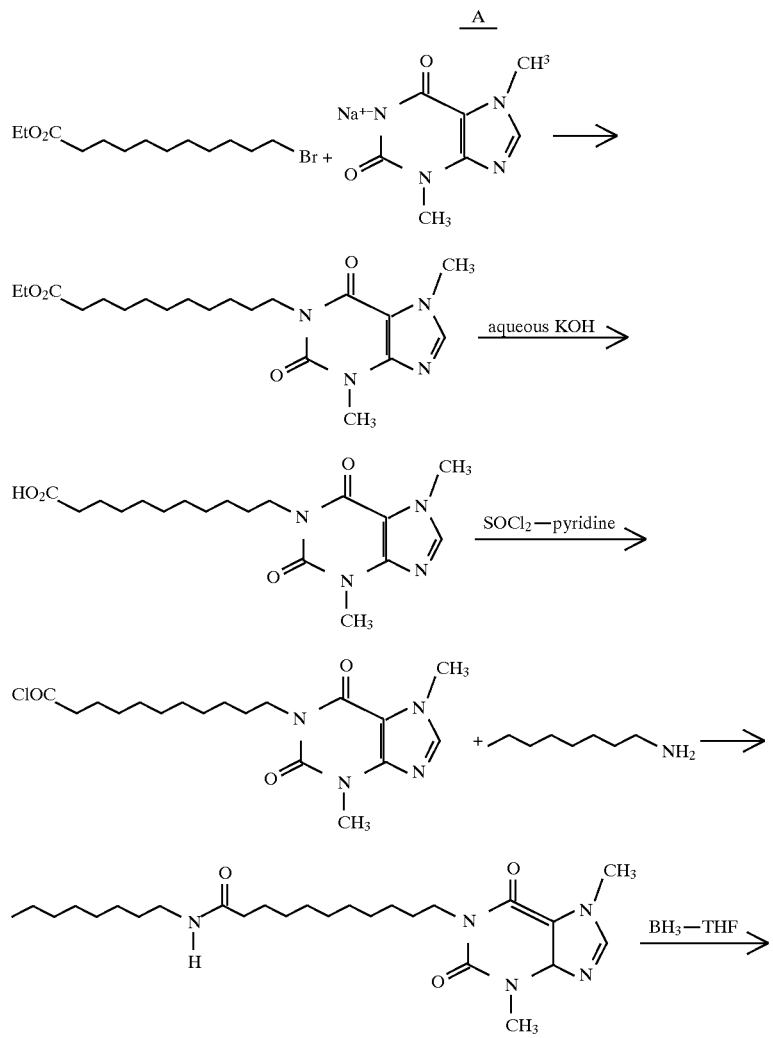

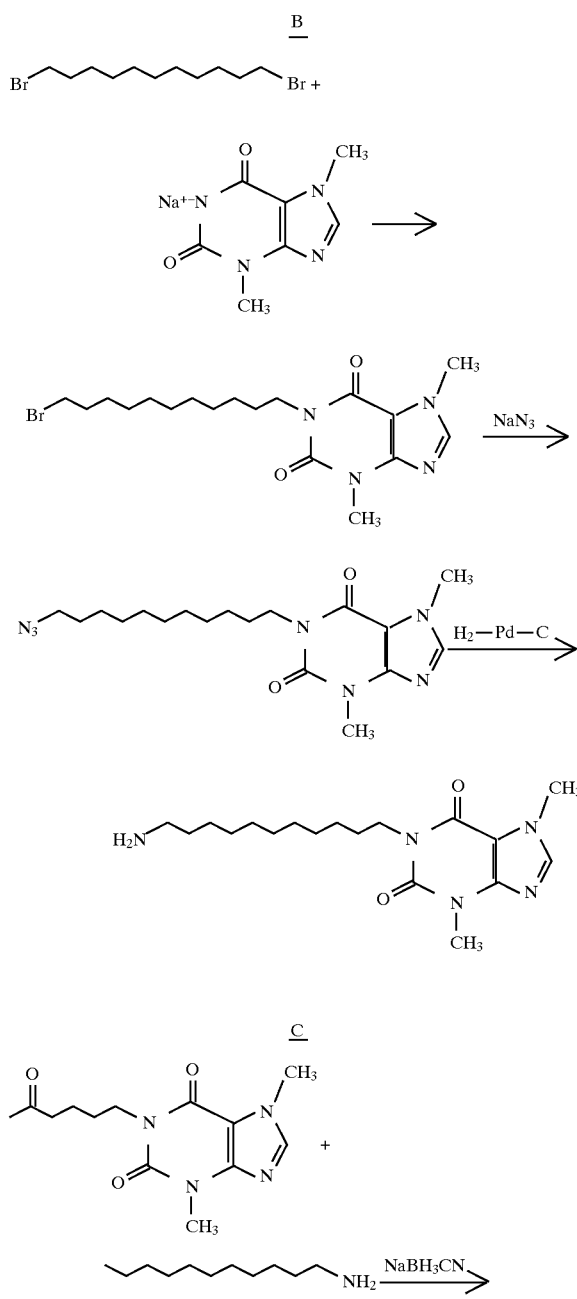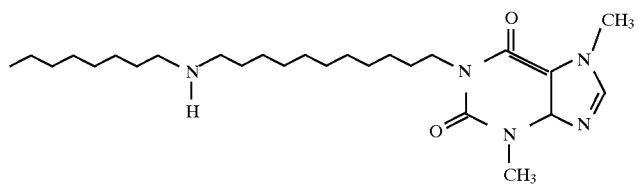

The compounds of the invention may be provided as enantiomeric or diastereomeric mixtures or in resolved or partially resolved forms. Standard procedures are used for resolving optical isomers. Different enantiomeric variants (e.g., stereoisomers and chiral forms) of the inventive compound may have different drug activities, based upon their differential ability to inhibit PAPH and LPAAT. An optical isomer, substantially free of the corresponding enantiomer and/or diastereomers, is at least about 85% of a relevant optical isomer, preferably at least about 95% relevant optical isomer and especially at least about 99% or higher relevant optical isomer. Most preferably an amount of other optical forms is undetectable.

The invention provides a pharmaceutical composition comprising an inventive compound and a pharmaceutically acceptable excipient. The pharmaceutical composition may be formulated for oral, parenteral or topical administration to a patient.

The invention further provides a pharmaceutical composition comprising an inventive compound and a pharmaceutically acceptable excipient, the pharmaceutical composition being formulated for oral, parenteral or topical administration to a patient. A pharmaceutical composition may alternatively comprise one or a plurality of inventive compounds and a pharmaceutically acceptable carrier or excipient. Treatment of individuals with the inventive compound or pharmaceutical composition may include, but limited to, contacting with the inventive compound in vitro culture, in an extracorporeal treatment, or by administering (oral, parenteral or topical) the inventive compound or pharmaceutical composition to a subject whose cells are to be treated.

Exemplary, preferred compounds of the invention include, but are not to, both R and S enantiomers and racemic mixtures of the following compounds:

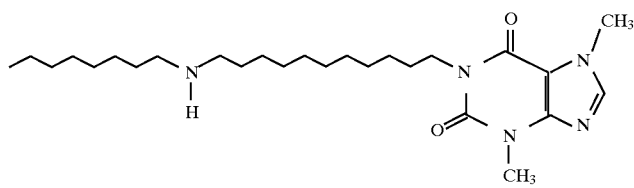
3556   1-(11-N-Octylaminoundecyl)-3,7-dimethylxanthine
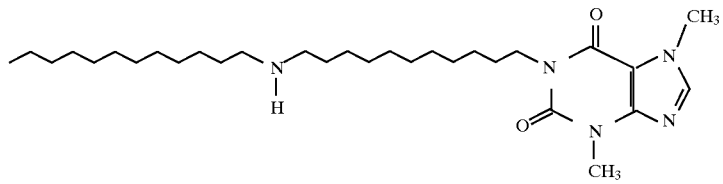
3563   1-(11-Dodecylaminoundecyl)-3,7-dimethylxanthine
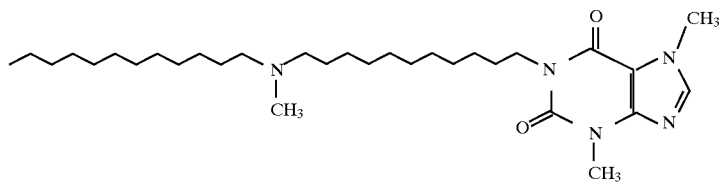
3576   1-[11-(N-Methyl-N-dodecylamino)undecyl]-3,7-dimethylxanthine
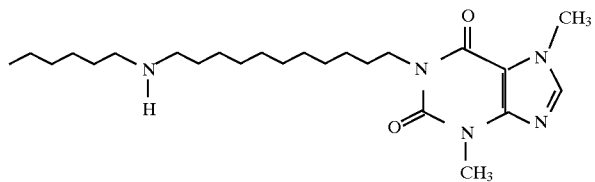
3580   1-(11-Hexylaminoundecyl)-3,7-dimethylxanthine
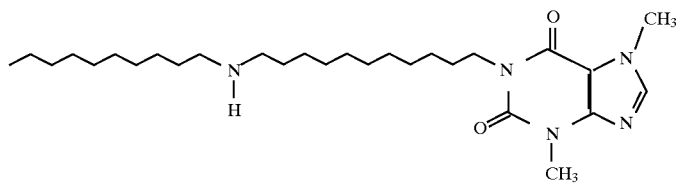
3581   1-(11-Decylaminoundecyl)-3,7-dimethylxanthine
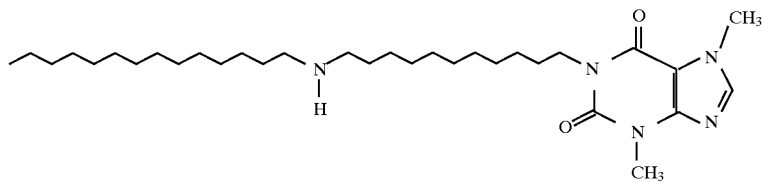
3582   1-(11-Tetradecylaminoundecyl)-3,7-dimethylxanthine
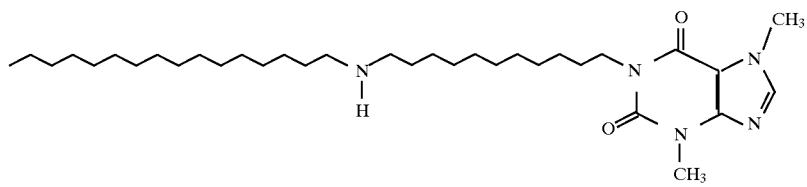
3584   1-(11-Hexadecylamioundecyl)-3,7-dimethylxanthine

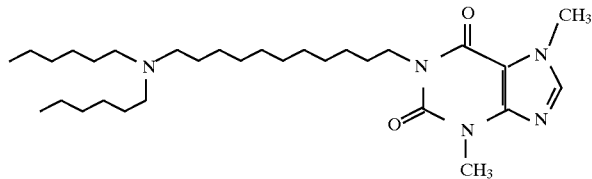
3590  1-[11-(N,N-Dihexylamino)undecyl]-3,6-dimethylxanthine
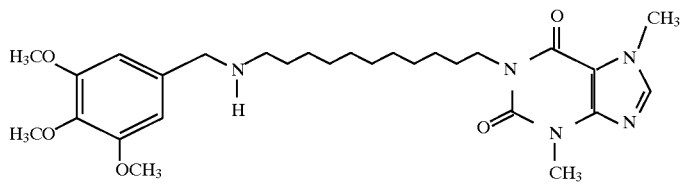
3593  1-[11-(3,4,5-Trimethoxybenylamino)undecyl]-3,7-dimethylxanthine
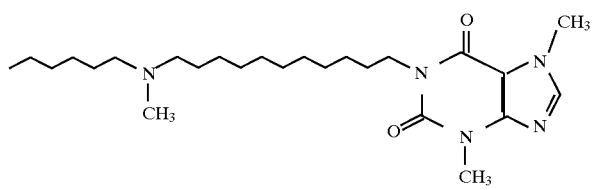
4500  1-[11-(N-Methyl-N-hexylamino)undecyl]-3,7-dimethylxanthine
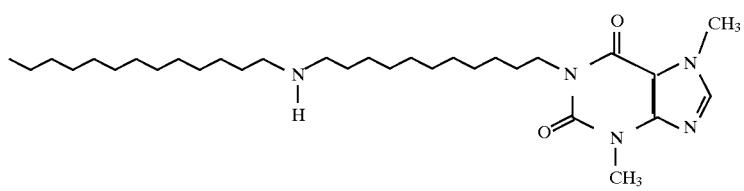
4507  1-(11-Tridecylaminoundecyl)-3,7-dimethylxanthine
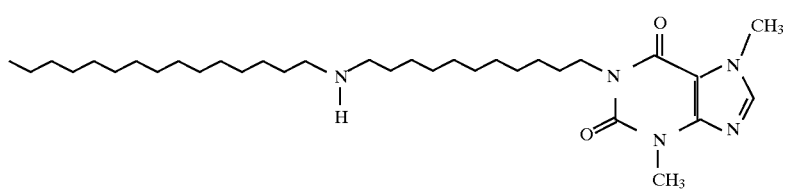
4508  1-(11-Pentadecylaminodecyl)-3,7-dimethylxanthine
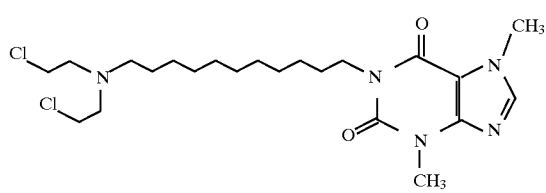
4505  1-[11-N,N-di(2-chloroethyl)aminoundecyl]-3,7-demethylxanthine
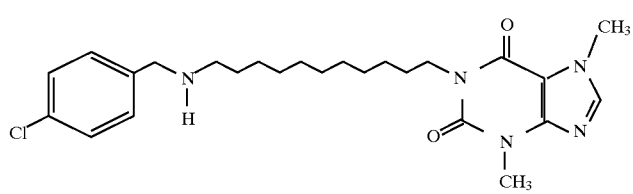
4569  1-(11-(4-Chlorobenzylamino)undecyl)-3,7-dimethylxanthine -continued
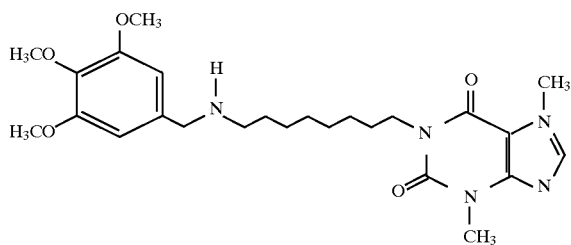
5574 1-[8-(3,4,5-Trimethoxybenzylamino)octyl]-3,7-dimethylxanthine
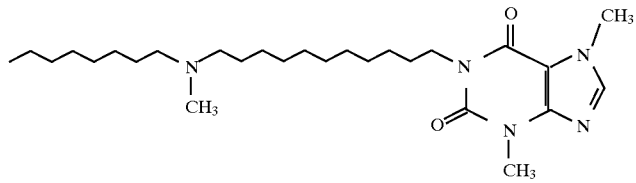
5589 1-[11-(Methyloctylamino)undecyl]-3,7-dimethylxanthine
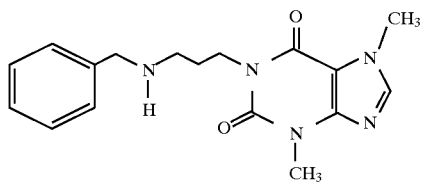
6503 1-(3-Benzylaminopropyl)-3,7-dimethylxanthine
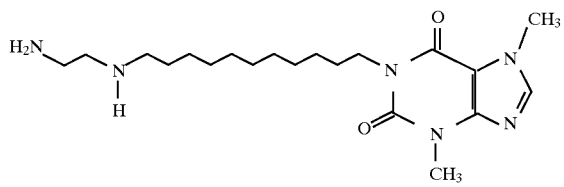
6504 1-[11-(2-aminoethyl)amino)undecyl]-3,7-dimethylxanthine
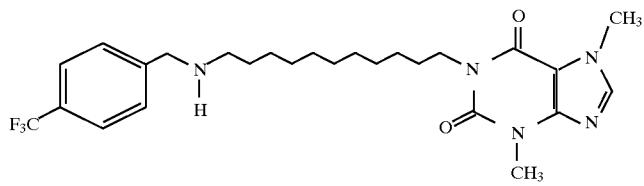
6510 1-[11-(4-Trifluoromethylbenzylamino)undecyl]-3,7-dimethylxanthine
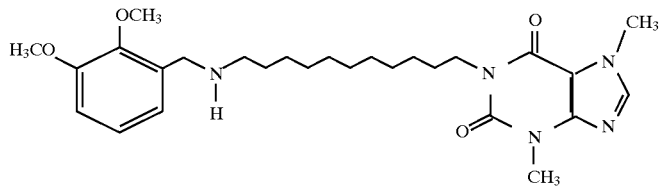
6513 1-[11-(2,3-Dimethoxybenzylamino)undecyl]-3,7-dimethylxanthine

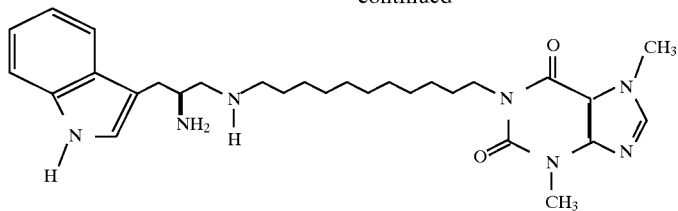
6515 1-[11-(2-amino-3-indolylpropylamino)undecyl]-3,7-dimethylxanthine
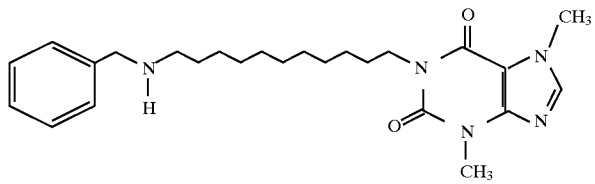
6531 1-[11-Benzylaminoundecyl]-3,7-dimethylxanthine
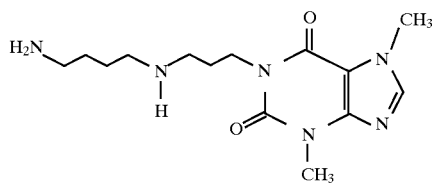
6532 1-(3-[4-Aminobutylamino]propyl)-3,7-dimethylxanthine
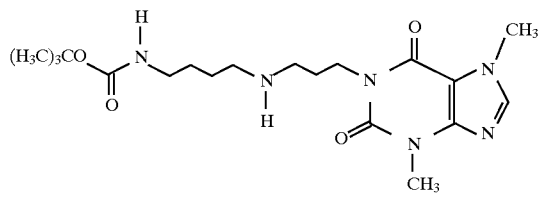
6533 1-(3-[4-Carbobutoxyaminobutylamino]propyl)-3,7-dimethylxanthine
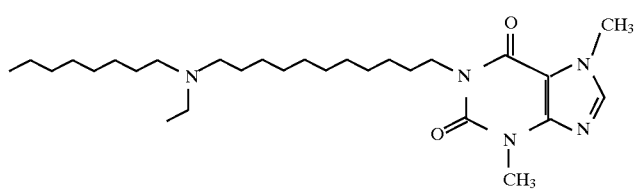
6534 1-(11-Ethyloctylaminoundecyl)-3,7-dimethylxanthine
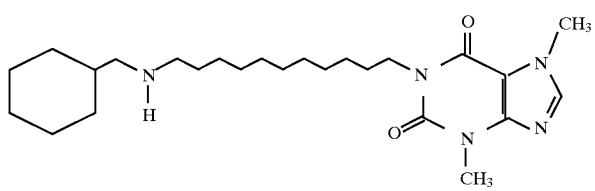
6542 1-[11-(Cyclohexylmethylamino)undecyl]-3,7-dimethylxanthine
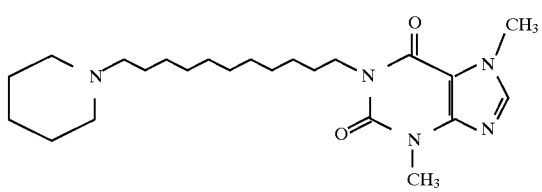
6543 1-[11-(Piperidinyl)undecyl]-3,7-dimethylxanthine

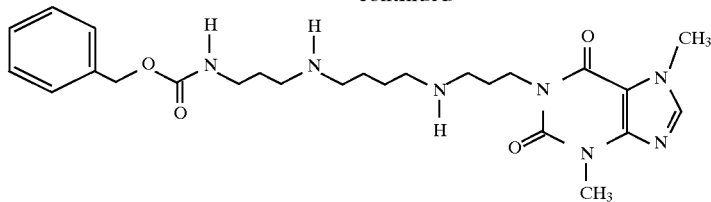

6552 1-(3-[4-(3-Carbobenzyloxyaminopropylamino)butylamino]propyl)-3,7-dimethylxanthine

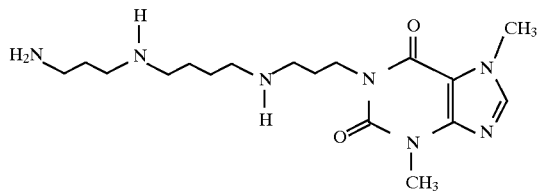

6553 1-(3-[4-(3-Aminopropylamino)butylamino]propyl)-3,7-dimethylxanthine

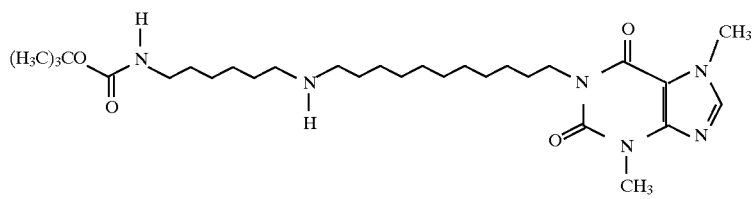

6555 1-(11-[6-Carbobutoxyaminohexylamio]undecyl)-3,7-dimethylxanthine

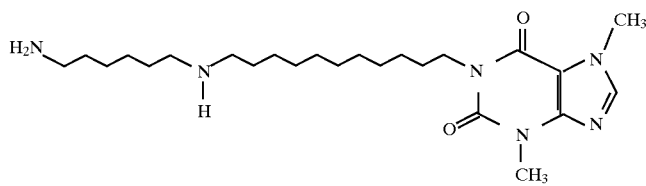

6556 1-(11-[6-Aminohexylamino]undecyl)-3,7-dimethylxanthine

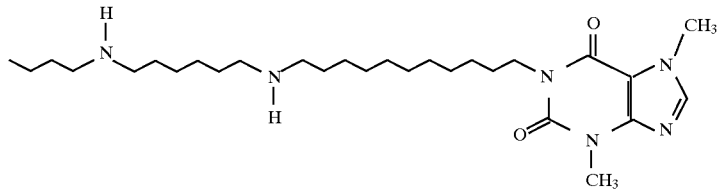

6557 1-(11-[6-Butylaminohexylamino]undecyl)-3,7-dimethylxanthine

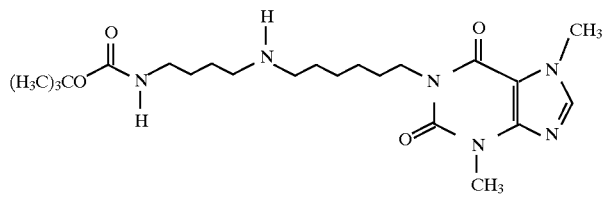

6558 1-(6-[4-Carbobutoxyaminobutylamino]hexyl)-3,7-dimethylxanthine

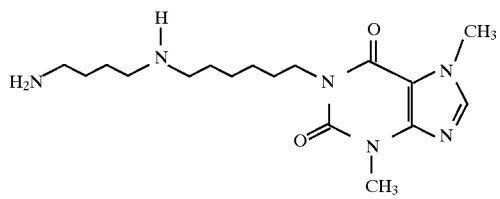

6559 1-(6-[4-Aminobutylamino]hexyl)-3,7-dimethylxanthine

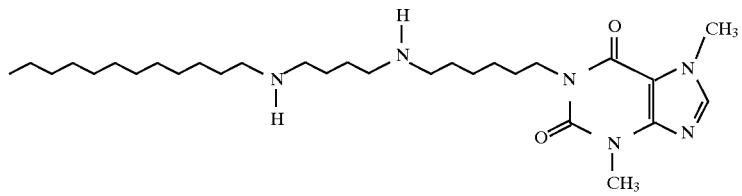

6560  1-(6-[4-Dodecylaminobutylamino]hexyl)-3,7-dimethylxanthine

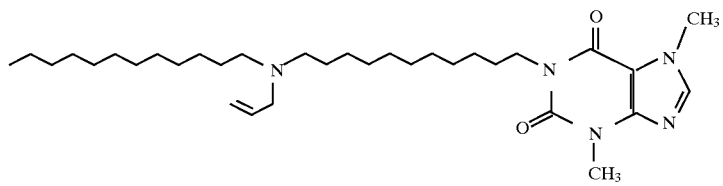

6563  1-(11-Allyldodecylaminoundecyl)-3,7-dimethylxanthine

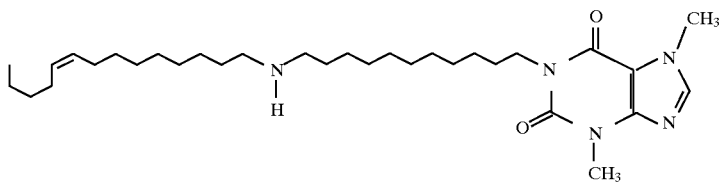

6570  1-[11-(cis-9-Tetradecenylamino)undecyl]-3,7-dimethylxanthine

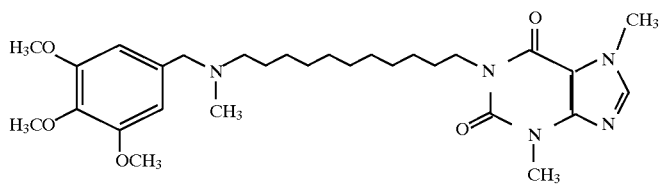

6571  1-[11-(N-Methyl-N-[3,4,5-trimethoxybenzyl]amino)undecyl]-3,7-dimethylxanthine

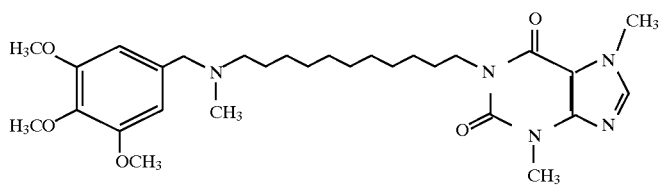

6576  1-(11-Dodecylethylaminoundecyl)-3,7-dimethylxanthine

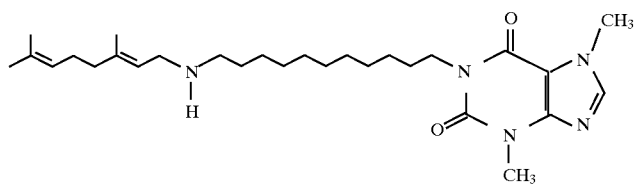

6579  1-[11-(trans-3,7-Dimethyl-2,6-octadienylamino)undecyl]-3,7-dimethylxanthine

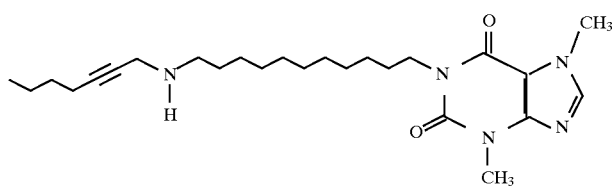

7510  1-{11-[(2-Heptyn-1-yl)amino]undecyl}-3,7-dimethylxanthine

-continued

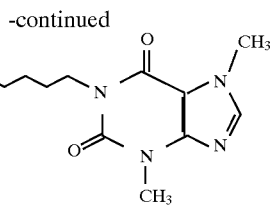

7511  1-{11-[(2-trans-Hepten-1-yl)amino]undecyl}-3,7-diemthylxanthine

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or nonaqueous carrier optionally containing a parenterally acceptable oil, for example polyethylene glycol, polyvinylpyrrolidone, lecithin, arachis oil, or sesame oil. The daily dosage for treatment of sepsis or another severe inflammatory condition by parenteral administration from about 0.001 mg/kg to about 40 mg/kg, preferably from about 0.01 mg/kg to about 20 mg/kg of an inventive compound or a pharmaceutically acceptable salt thereof, calculated as the free base.

The inventive compounds may be administered orally. The daily dosage regimen for oral administration is suitably from about 0.1 mg/kg to about 1000 mg/kg per day. For administration the dosage is suitably form about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral). Appropriate dosage forms include, but is not limited to, an aerosol or a metered dose inhaler, as prepared by conventional techniques. The daily dosage is suitably form about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

While dosage values will vary, therapeutic efficacy is achieved when the compounds of the invention are administered to a human subject requiring such treatment as an effective oral, parenteral, or intravenous dose of about 50 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

The following examples, which should not be regarded as limiting in any way, further illustrate the invention.

EXAMPLE 1

This example is a method of synthesis for inventive compound no. 3506 (see above for chemical name and structure). A mixture of theobromine (1.0 g, 5.5 mmol, available from Sigma) and 50% sodium hydride in oil (264 mg, 5.5 mmol) in dimethylsulfoxide (20 ml) was stirred for 50 minutes and then 6-bromo-1-hexanol (1.0 g, 5.5 mmol, available from Aldrich) was added. After stirring for 18 hours, the solution was treated with water (50 ml) and then extracted with two 25 ml aliquots of hexanes. The aqueous phase was extracted with three 35 ml aliquots of 25% ethanol-dichloromethane. The combined ethanol-dichloromethane extracts were dried over magnesium sulfate. The solvents were then evaporated under vacuum and remaining dimethylsulfoxide was removed by distillation under full pump vacuum, leaving 1.4 g of a white powder, 1-(6-hydroxyhexyl)-3,7-dimethylxanthine (5.0 mmol, 91% yield).

Dimethyl sulfoxide (156 µl, 172 mg, 2.2 mmol) was slowly added to a solution of oxalyl chloride (103 µl, 150 mg, 1.2 mmol) in dichloromethane at −78° C. A solution of 1-(6-hydroxyhexyl)-3,7-dimethylxanthine (300 mg, 1.1 mmol), prepared in the previous step, in dichloromethane (5 ml) was added to this solution and the resulting reaction mixture stirred for 15 minutes. The cold bath was removed after addition of triethylamine (765 µl, 555 mg, 5.5 mmol). The reaction was added at ambient temperature to 20 ml water and extracted with three 50 ml aliquots of methylene chloride. The combined organic layers were washed with 1% aqueous hydrogen chloride (20 ml), saturated aqueous sodium bicarbonate (20 ml), and saturated aqueous salt solution (20 ml), and then dried over sodium sulfate. Evaporating the solvents and recrystallizing a residue in chloroform/petroleum ether produced 267 mg of 1-(6-oxohexyl)-3,7-dimethylxanthine (87% yield).

Then, sodium cyanoborohydride (63 mg, 1.0 mmol) was added to a mixture of 1-(6-oxohexyl)-3,7-dimethylxanthine (150 mg, 0.5 mmol), prepared above, undecylamine (0.43 ml, 2.5 mmol), 38% aqueous hydrochloric acid solution (0.2 ml, 2.5 mmol), methanol (5 ml), and THF (5 ml) and the resulting solution stirred for 48 hours. Saturated aqueous ammonium chloride solution (20 ml) was added to the stirring solution. Following an additional 20 minutes of stirring, 30 ml of 30% aqueous ammonium hydroxide solution were added. The mixture was extracted with three 35 ml aliquots of 25% methanol-dichloromethane. The combined extracts were dried over sodium sulfate and the solvents were evaporated under vacuum, producing 190 mg of compound no. 3506 (86% yield).

EXAMPLE 2

This example is a method of synthesis for inventive compound no. 3556. A solution of 11-bromoundecanoic acid (available from Aldrich, 5.70 g, 22 mmol) and p-toluenesulfonic acid (0.1 g) in absolute ethanol (100 ml) was refluxed for 3 hours. Saturated aqueous sodium bicarbonate solution (40 ml) was added and the reaction mixture was extracted with dichloromethane (3×70 ml). The combined extracts were washed with water (50 ml) and saturated aqueous salt solution (50 ml), and then the solvent was evaporated to a colorless oil. Ethyl 11-bromoundecanoate (5.92 g, 94% yield) was collected during distillation (2 mm) at 135° C. A solution of the bromoester (5.92 g, 20 mmol) and 1-sodiotheobromine (4.08 g, 20 mmol) in dimethylsulfoxide (80 ml) was stirred for 18 hours at ambient temperature. The mixture was added to water (100 ml) and dichloromethane (100 ml). The aqueous layer was extracted with dichloromethane (2×80 ml). The combined organic layers were washed with water (80 ml) and saturated aqueous salt solution (80 ml), dried over magnesium sulfate, and evaporated under vacuum to a white solid. The residue was recrystallized in dichloromethane/ether/hexane, yielding 4.95 g of 1-(ethyl 11-yl-undecanoate)-3,7-dimethylxanthine (62% yield).

A solution of potassium hydroxide (0.50 g, 9.0 mmol) in water (1 ml) was added to a stirring suspension of 1-(ethyl 11-yl-undecanoate)-3,7-dimethylxanthine (2.52 g, 6.4 mmol) in methanol (15 ml). The mixture was warmed until it became homogeneous, and the stirring was continued overnight at ambient temperature. Water (10 ml) was added to the reaction mixture followed by a 5% solution of sulfuric acid (10 ml). The precipitate was filtered off and washed with ether, then dried under vacuum to obtain 2.12 g of 1-(11-yl-undecanoic acid)-3,7-dimethylxanthine (91% yield).

A solution of 1-(11-yl-undecanoic acid)-3,7-dimethylxanthine (1.62 g, 4.5 mmol) and thionyl chloride (0.5 ml, 6.7 mmol) in toluene (5 ml) was heated at 80° C. for 1 hour and then cooled. The solvent was evaporated under a nitrogen stream. The resulting acid chloride was taken up in dichloromethane (20 ml), and 1-octylamine (2 ml, 11 mmol) was added by syringe to the stirring solution. After 2 hours, water (50 ml) was added and the mixture was extracted with three 50 ml aliquots of dichloromethane. The combined organic extracts were washed with 5% hydrochloric acid (100 ml) and saturated aqueous salt solution (60 ml) and then dried over sodium sulfate. The solvent was evaporated under vacuum, leaving a residue was purified by column chromatography using basic activity II alumina and a dichloromethane/10% methanol eluant producing 1.47 g of white solid, 1-(N-octyl 11-yl-undecanamide)-3,7-dimethylxanthine (69% yield).

A 1M solution of borane-tetrahydrofuran (6 ml, 6 mmol) was added dropwise to a stirring solution of 1-(N-octyl-11-yl-undecanoamide)-3,7-dimethylxanthine (0.85 g, 1.8 mmol), prepared above, in tetrahydrofuran (10 ml) under argon. After 3 hours of stirring at reflux, the reaction mixture was cooled to ambient temperature and 6M aqueous hydrogen chloride (4 ml) was added dropwise, resulting in a foaming reaction mixture. After bubbling subsided, most of the solvent was removed under a stream of argon. Water (20 ml) was added, and saturated aqueous sodium bicarbonate solution was added dropwise until the aqueous mixture was at a Ph of approximately 8, using Ph paper to test. The mixture was extracted with three 40 ml aliquots of dichloromethane. The combined organic layers were evaporated under vacuum, leaving a white solid residue. This residue was purified by column chromatography using neutral activity II alumina and a dichloromethane/3% methanol eluant, producing 0.66 g of a white solid, 1-(11-octylaminoundecyl)-3,7-dimethylxanthine (80% yield).

EXAMPLE 3

This example is a method of synthesis for inventive compound no. 3563 (see above for chemical name and number). 1-(11-Y1-undecanoic acid)-3,7-dimethylxanthine was prepared as described in the synthetic protocol of example 2. Thionyl chloride (0.6 ml, 8.2 mmol) was added to a slurry of 1-(11-yl-undecanoic acid)-3,7-dimethylxanthine (2.12 g, 5.8 mmol) in toluene (5 ml) under argon. The stirring mixture was warmed to 80° C., and became homogeneous. After 1 hour, the solvent was evaporated under a stream of argon, to give the acid chloride as an off-white solid residue. This compound was used in the next step without further purification. The acid chloride was taken up in dichloromethane (20 ml) and added dropwise to a stirring solution of dodecylamine (4.3 g, 23 mmol) in dichloromethane (20 ml). After 2 hours of stirring at ambient temperature, 3% aqueous hydrogen chloride solution (100 ml) and water (50 ml) was added to the resulting slurry. The mixture was extracted with dichloromethane-5% methanol (3×70 ml). The combined organic layers were washed with saturated aqueous salt solution (70 ml) and dried over magnesium sulfate. The solvents were evaporated under vacuum to give a white solid residue. The solid was purified by column chromatography (silica/dichloromethane-5% methanol), yielding 2.08 g of a white solid, 1-(N-dodecyl-11-yl-undecanoamide)-3,7-dimethylxanthine (68% yield).

A 1M solution of borane-tetrahydrofuran (2 ml, 2 mmol) was added dropwise to a stirring solution of 1-(N-dodecyl-11-yl-undecanoamide)-3,7-dimethylxanthine (0.30 g 0.6 mmol), prepared above, in tetrahydrofuran (5 ml) under argon. After 2 hours of stirring at reflux, the reaction mixture was cooled to ambient temperature and 6M aqueous hydrogen chloride (0.6 ml) was added dropwise. After bubbling subsided, the solvent was mostly removed under a stream of argon. Water (10 ml) and dichloromethane (20 ml) was added, and saturated aqueous sodium hydroxide solution was dripped in until the aqueous layer showed a Ph of approximately 10 using pH paper. The organic layer was separated and the aqueous layer was extracted with dichloromethane (2×60 ml). The combined organic layers were evaporated under vacuum to a white solid. This residue was purified by chromatography (neutral activity II alumina, dichloromethane-3% methanol), resulting in 240 mg of a white solid, inventive compound no. 3563 (77 % yield).

EXAMPLE 4

This example is a method of synthesis for inventive compound no. 4500. To a slurry of 1-(11-yl-undecanoic acid)-3,7-dimethylxanthine (2.0 g, 5.5 mmol), prepared as an intermediate in example 2, in toluene (10 ml) under argon was added thionyl chloride (0.6 ml, 8.2 mmol). The stirring mixture was warmed to 80° C., and became homogeneous. After 1 hour, the excess thionyl chloride was removed under a stream of argon and the solvent was removed under reduced pressure, to give the acid chloride as an off-white solid. This compound was used in the next step without further purification. The acid chloride was taken up in dichloromethane (20 ml) and added dropwise to a stirring solution of 1-hexylamine (2.1 ml, 16 mmol) in dichloromethane (20 ml). After 2 hours of stirring at ambient temperature, the reaction was poured into 3% aqueous hydrogen chloride solution (100 ml) followed by saturated aqueous salt solution (40 ml). The mixture was extracted with dichloromethane (3×50 ml). The combined organic layers were washed with saturated aqueous salt solution (50 ml) and dried over magnesium sulfate. The solvents were evaporated under vacuum to give a white solid residue. The solid obtained was purified by column chromatography (silica/dichloromethane-5% methanol), resulting in 1.52 g of a white solid, 1-(N-hexyl-11-yl-undecanamide)-3,7-dimethylxanthine (62% yield).

To a stirring solution of 1-(N-hexyl-11-yl-undecanamide)-3,7-dimethylxanthine (1.0 g, 2.3 mmol), prepared above, in tetrahydrofuran (15 ml), cooled to 0° C. under argon was slowly added borane-tetrahydrofuran complex (6.7 ml, 6.7 mmol). The cold bath was removed and the reaction was heated to 70° C. After 3 hours the reaction was cooled to ambient temperature and 6 molar hydrochloric acid (6 ml) was slowly added. The tetrahydrofuran was removed by distillation at atmospheric pressure. To the remaining cooled aqueous solution was added dichloromethane (30 ml), a saturated solution of sodium hydroxide (10 ml) and water (20 ml). The basic aqueous solution was extracted with dichloromethane (3×25 ml). The organic extracts were dried over anhydrous sodium sulfate. Removal of solvent under reduced pressure gave a crude white residue. Column chromatography on neutral activity II alumina (ethyl acetate/ 10% methanol) yielded 0.71 g of 1-(11-hexylaminoundecyl)-3,7-dimethylxanthine (73% yield) as a white solid.

Formic acid (0.23 ml, 6.1 mmol) was added to 1-(11-hexylaminoundecyl)-3,7-dimethylxanthine (300 mg, 0.7 mmol), prepared above. A 37% aqueous solution of formaldehyde (0.41 ml, 5.4 mmol) was added and the reaction solution was stirred at 90° C. for 24 hours. After cooling to ambient temperature, a saturated solution of sodium carbonate (15 ml) was added. The basic aqueous solution was extracted with dichloromethane (3×15 ml). The organic extracts were collected and dried over anhydrous magnesium sulfate. Solvent was removed under reduced pressure to give a crude yellow oil. Column chromatography on neutral activity alumina with ethyl acetate/10% methanol/ 10% trimethylamine as eluant produced 180 mg of a colorless oil, which solidified upon standing, inventive compound no. 4500 (180 mg, 54% yield).

EXAMPLE 5

This example shows the effects of inventive compound no. 3506 on PDGF-induced proliferation in human stromal cells. Procedurally, human stromal cells were starved in serum-free media for 24 hours and then stimulated with 50 ng/ml PDGF. Compound no. 3506 was added at various concentrations one hour prior to PDGF stimulation and pulsed for 24 hours. Cells were harvested and cell proliferation measured having background counts (i.e., starved cells) at about 10% of control levels. FIG. 1 illustrates the inventive compound's inhibition of PDGF-induced proliferation at various concentrations ($\mu$M).

EXAMPLE 6

This example illustrates inhibitive effects of the inventive compounds on Balb/3T3 cell proliferation in response to platelet derived growth factor (PDGF) stimulation.

Disregulated PDGF-proliferative response has been linked to a variety of diseases, including, e.g., restenosis, atherosclerosis, fibrosis, and tumor cell angiogenesis. Balb/3T3 cells respond vigorously to PDGF stimulation, and are useful in vitro models for further study of PDGF-induced proliferation. In an assay useful in determining whether a compound would be useful in treating diseases characterized by this or similar disregulated proliferative responses, research indicates that the inventive compounds inhibit PDGF-induced proliferation of Balb/3T3 cells.

Figure 2:
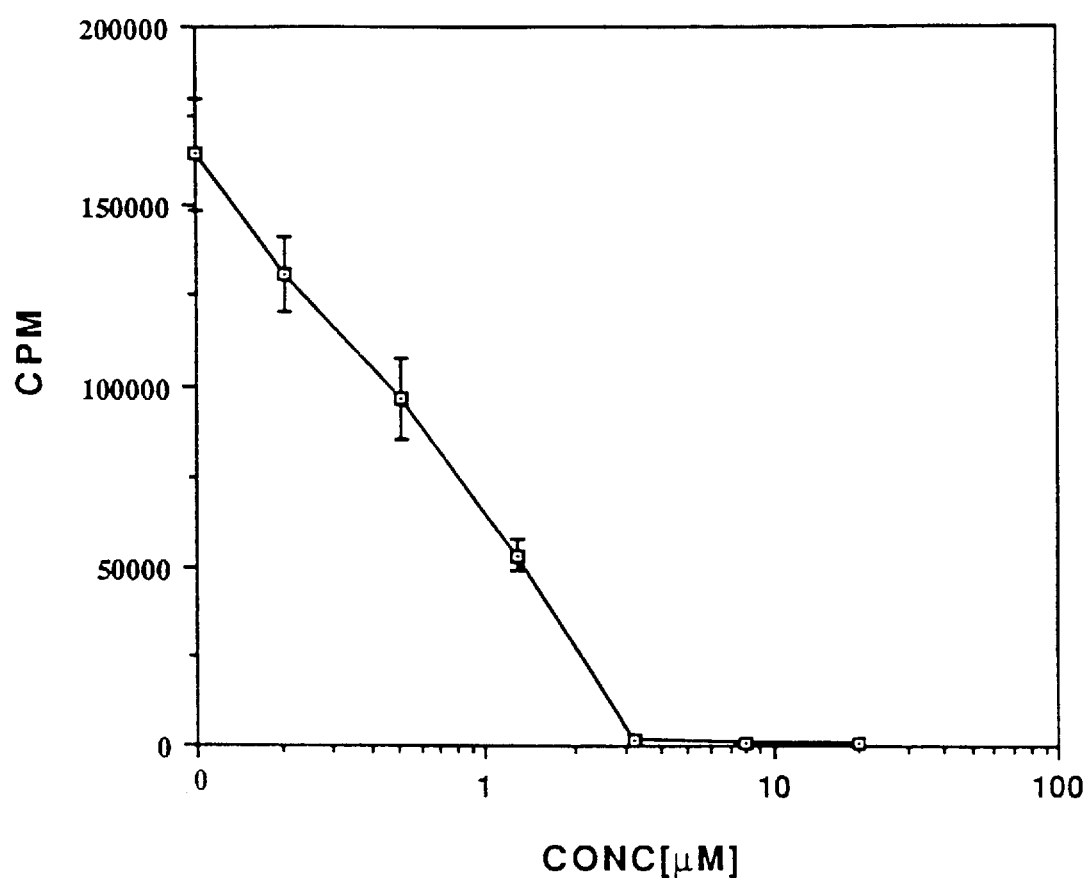
FIG. 2 illustrates inhibitive effects of inventive compound no. 3556 on proliferation of Balb/3T3 cells, stimulated with PDGF.
Figure 4:
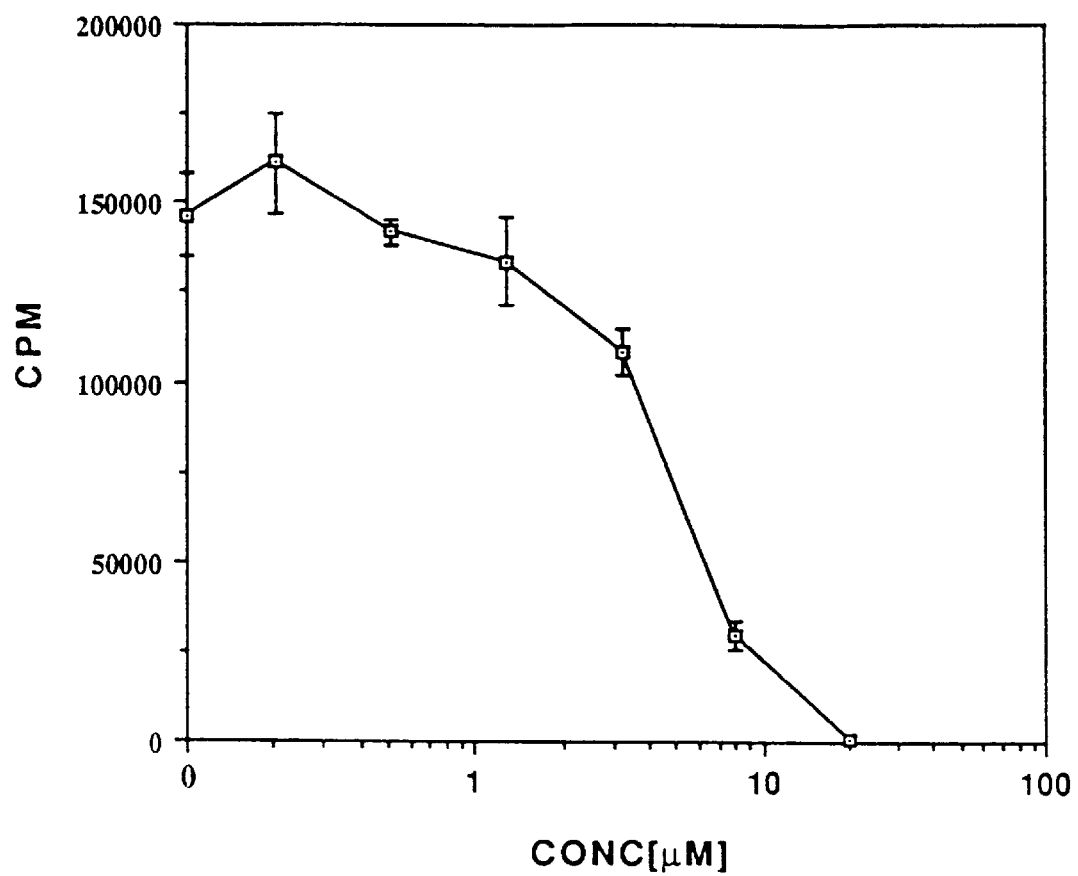
FIG. 4 illustrates inhibitive effects of inventive compound no. 4500 on proliferation of Balb/3T3 cells, stimulated with PDGF.

Balb/3T3 cells were plated in low serum-containing medium for 24 hours prior to stimulation with various concentrations of inventive compounds nos. 3556 and 4500. PDGF was added at varying concentrations along with tritiated thymidine. The cells were allowed to incubate for one day, following addition of PDGF and thymidine. Twenty-four hours later, the cells were harvested and counted by liquid scintillation counting. FIGS. 2 and 4 report data for inventive compounds nos. 3556 and 4500, respectively, obtained in this proliferation assay. The results shown in each respective figure illustrate that inventive compounds nos. 3556 and 4500 inhibit proliferation of Balb/3T3 cells stimulated by PDGF at concentrations less than 30 $\mu$M, indicating that the inventive compounds are candidates for treating or preventing restenosis, atherosclerosis, fibrosis, tumor cell angiogenesis and other similar diseases.

Figure 3:
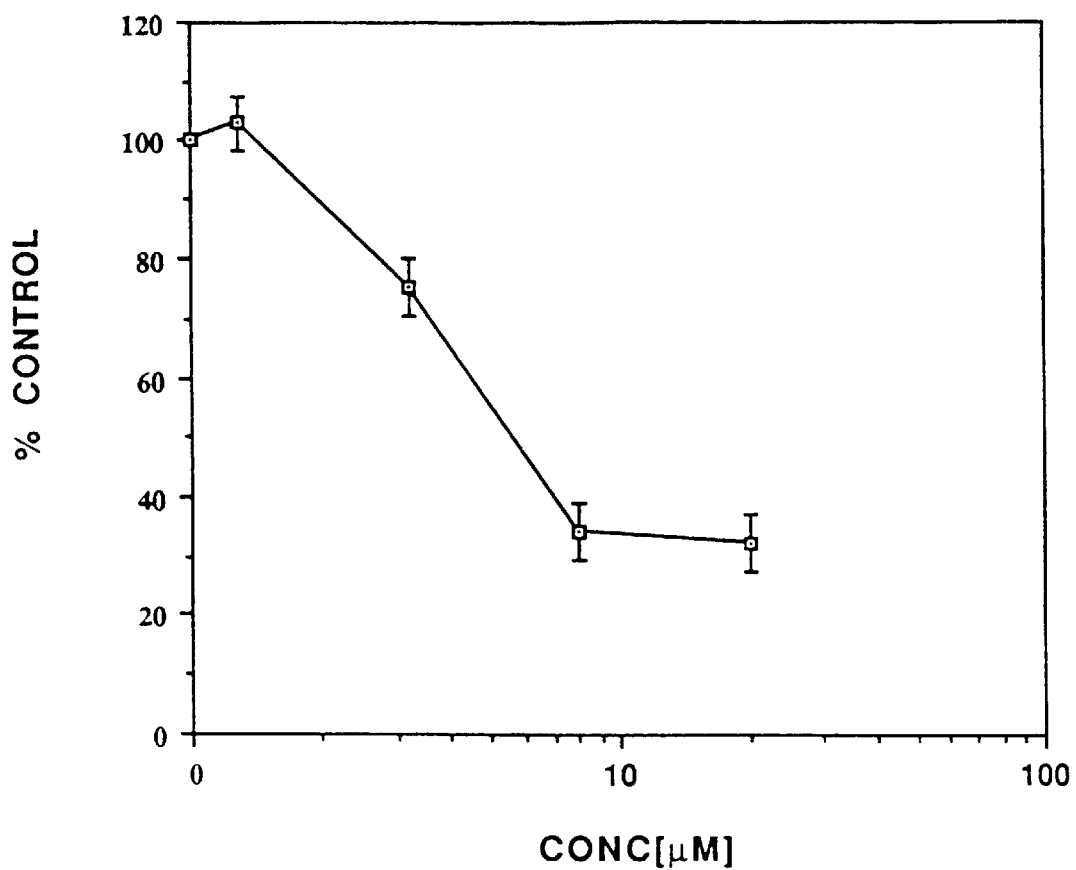
FIG. 3 reports cytotoxicity data obtained in the PDGF assay used to obtain data reported in FIG. 1 for compound no. 3556.
Figure 5:
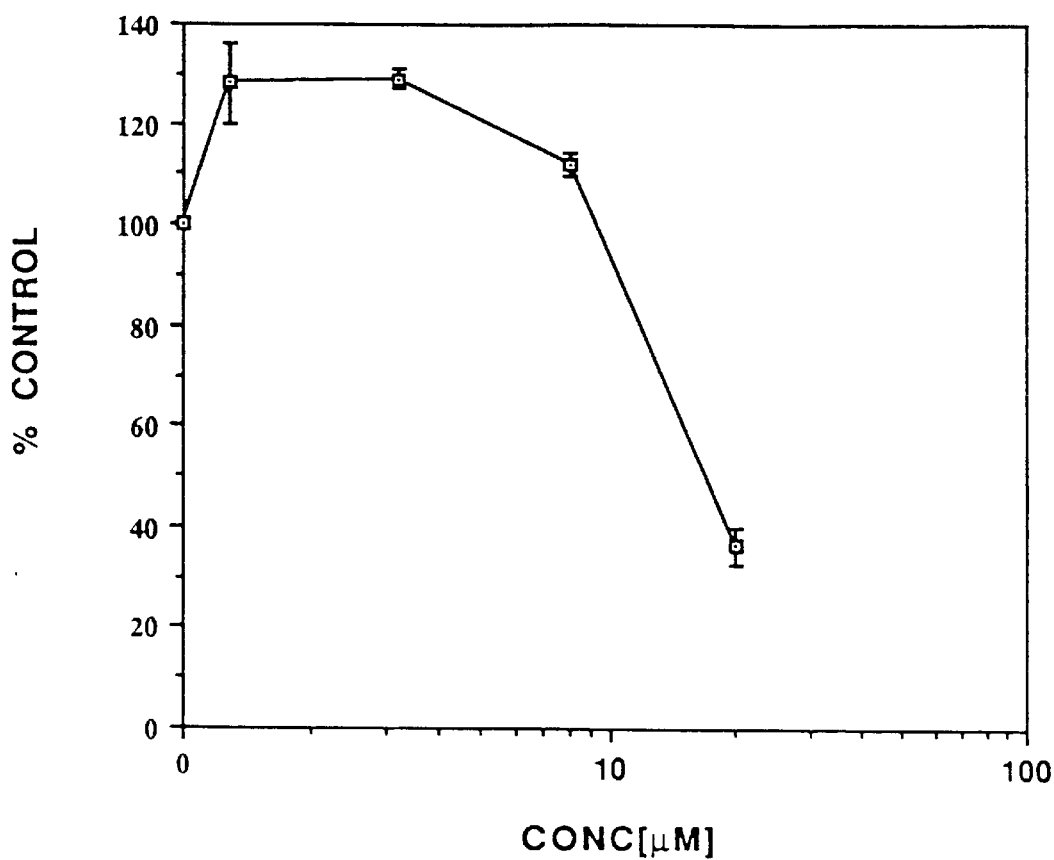
FIG. 5 reports cytotoxicity data obtained in the PDGF assay used to obtain data reported in FIG. 4 for compound no. 4500.

In conjunction with the Balb/3T3 proliferation assay, a related viability assay was conducted to assess the cytotoxicity of compounds which inhibit proliferation in this system. The assay protocol was identical to that performed above except that tritiated thymidine was not added after the 24 hour incubation with PDGF. In this cytotoxicity assay, after incubating the cells, a 10 $\mu$M solution of BCECF was added and the cells were incubated for 30 minutes at 37° C. Following this incubation, BCECF was replaced with PBS and the plate read for fluorescence in a Millipore cytofluorometer. Data obtained was plotted as a percent of control versus concentration of inventive compound tested. FIGS. 3 and 5 represent the results of this viability assay, for compounds nos. 3556 and 4500, respectively. The compounds tested (compounds nos. 3556 and 4500) were not cytotoxic to any cells (as compared with a control value of 100%) at concentrations shown in FIGS. 1, 2 and 4, the concentrations at which the respective compounds inhibit proliferation.

EXAMPLE 7

This example shows an inhibitive effect of inventive compounds nos. 3506, 3556, 3563, 3576, 3581, 3582 and 3584 on thymocyte proliferation and activation, co-stimulated with Concanavalin A (Con A) and interleukin-2 (IL-2), at various concentrations of the compounds ($IC_{50}$). Con A and IL-2 together stimulate T cell proliferation and differentiation.

Figure 6:
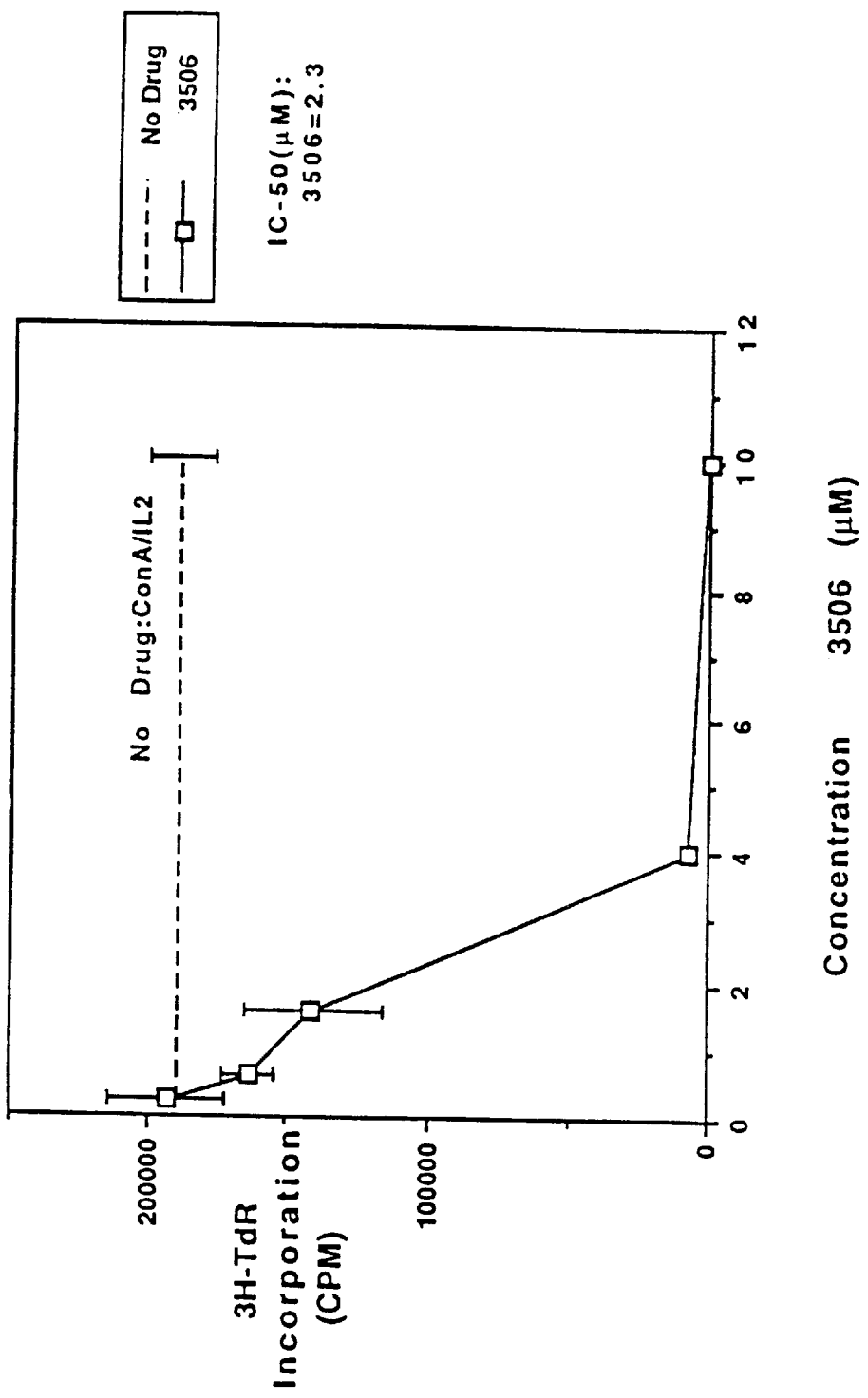
FIGS. 6, 7, 8, 9, 10 and 11 report results obtained for inventive compounds nos. 3506, 3556, 3563, 3576, 3581, 3582 and 3584 in a thymocyte proliferation assay in which thymocytes were co-stimulated with Con A and IL-2 and proliferation of thymocytes was measured.
Figure 7:
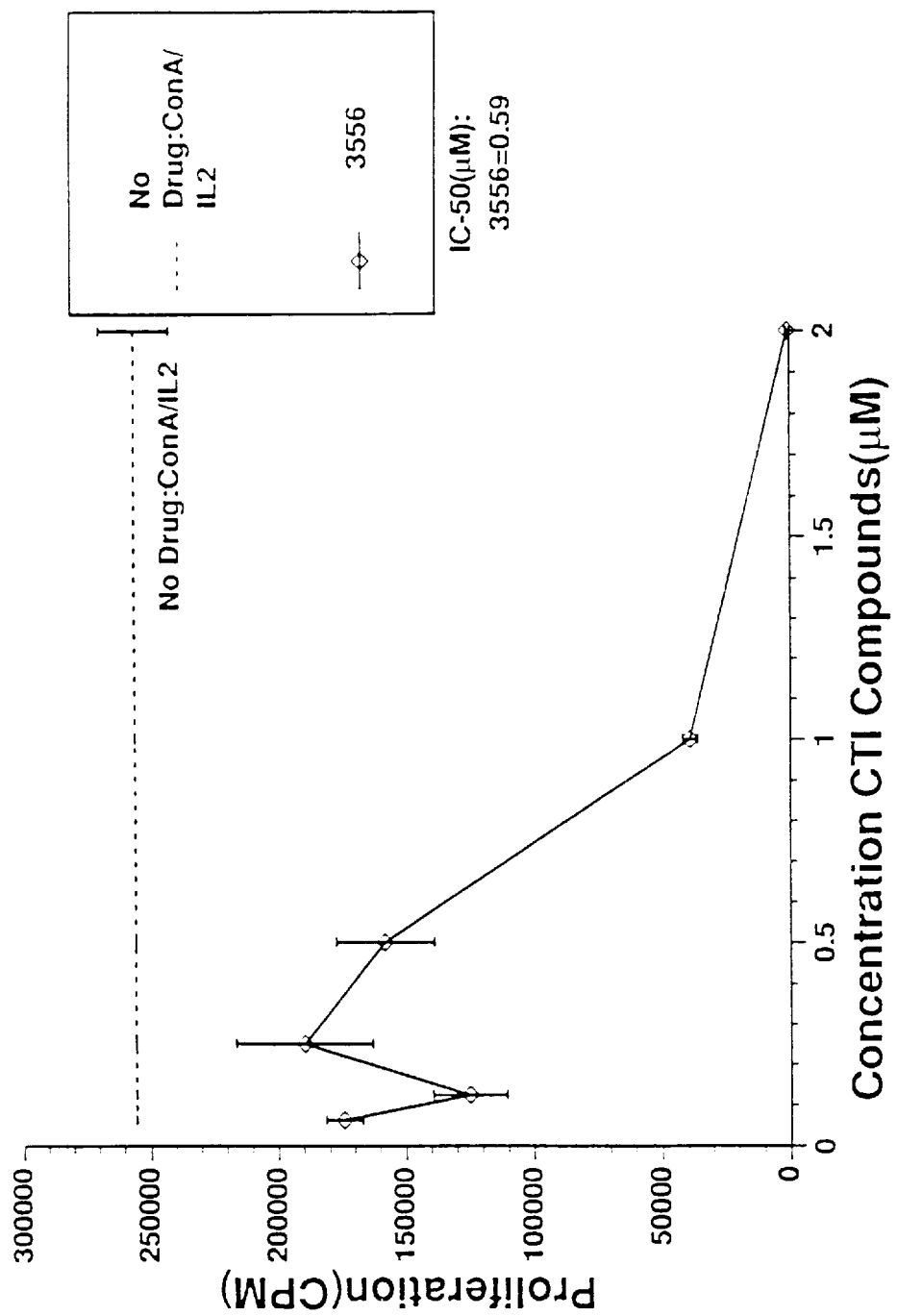
Figure 8:
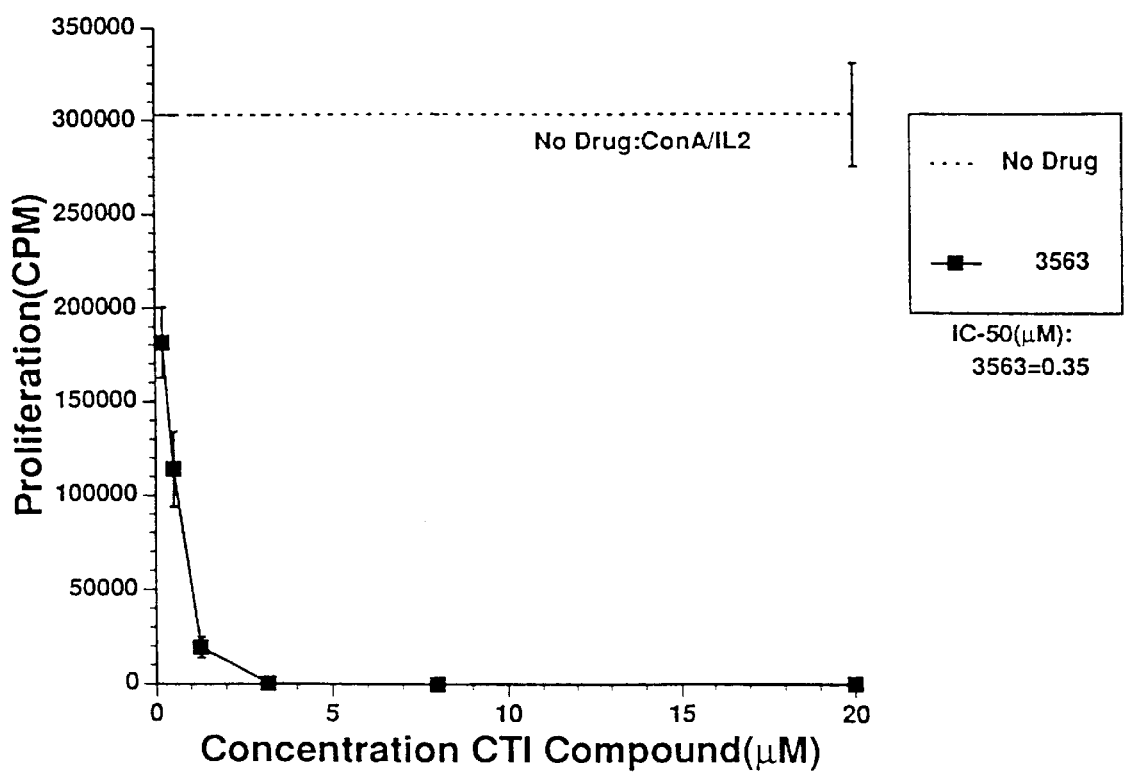
Figure 9:
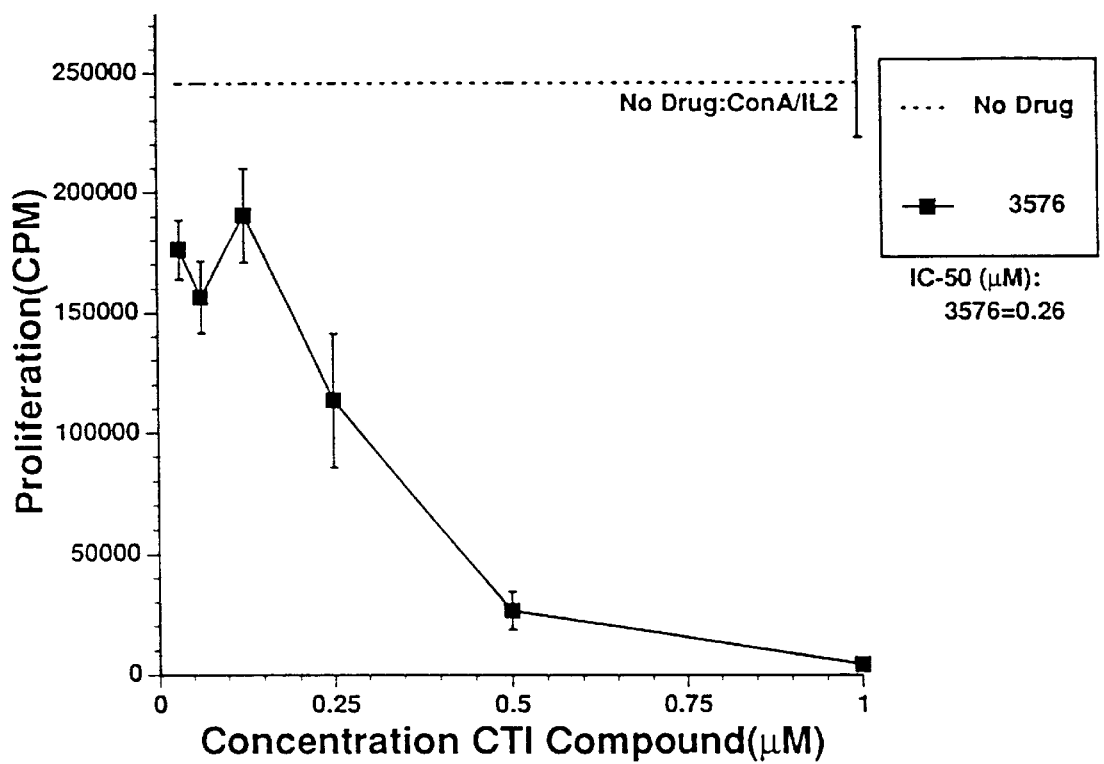
Figure 10:
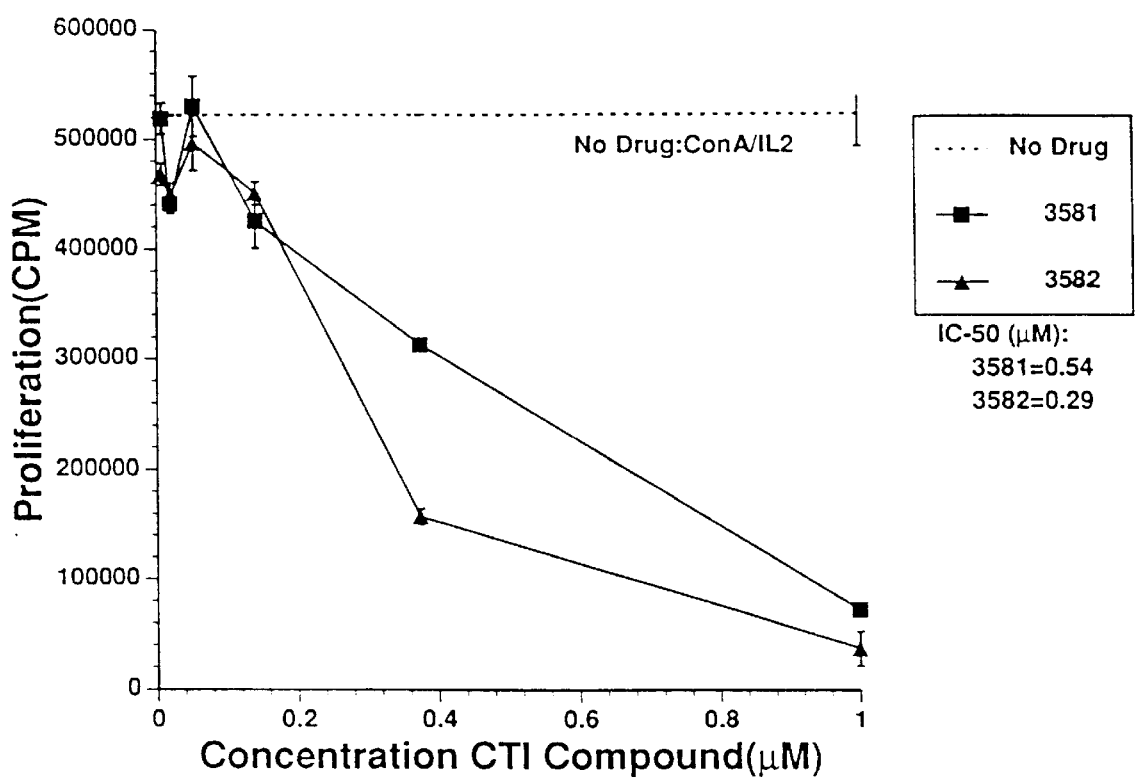
Figure 11:
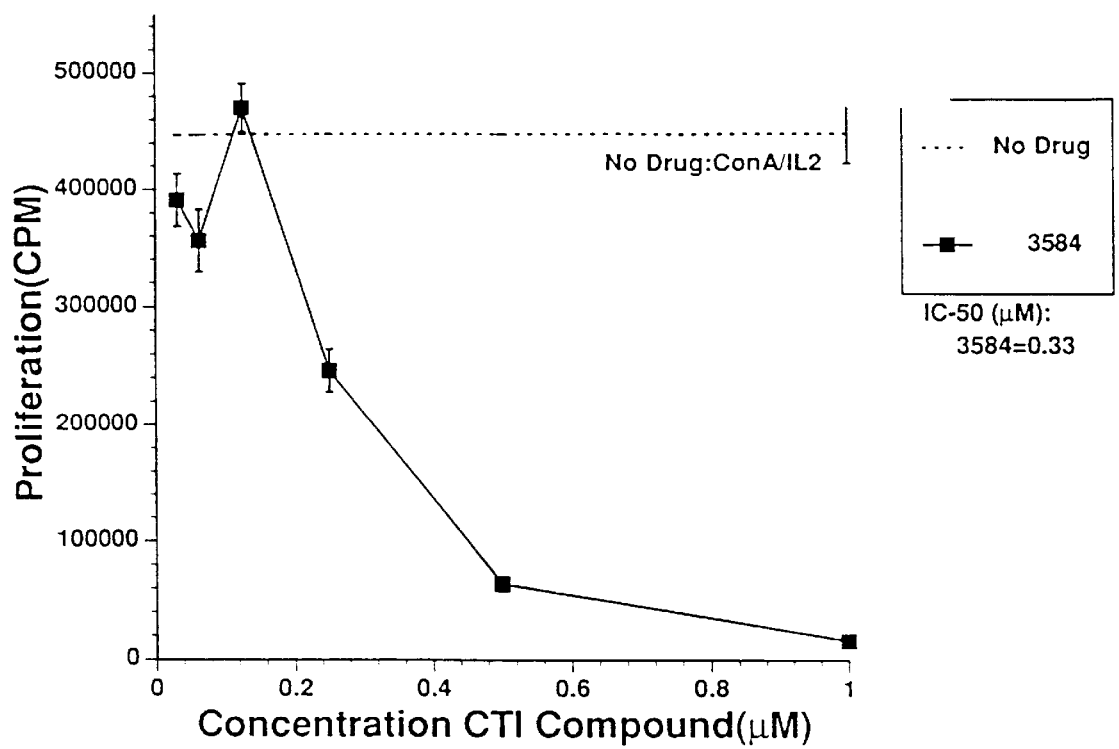
Figure 12:
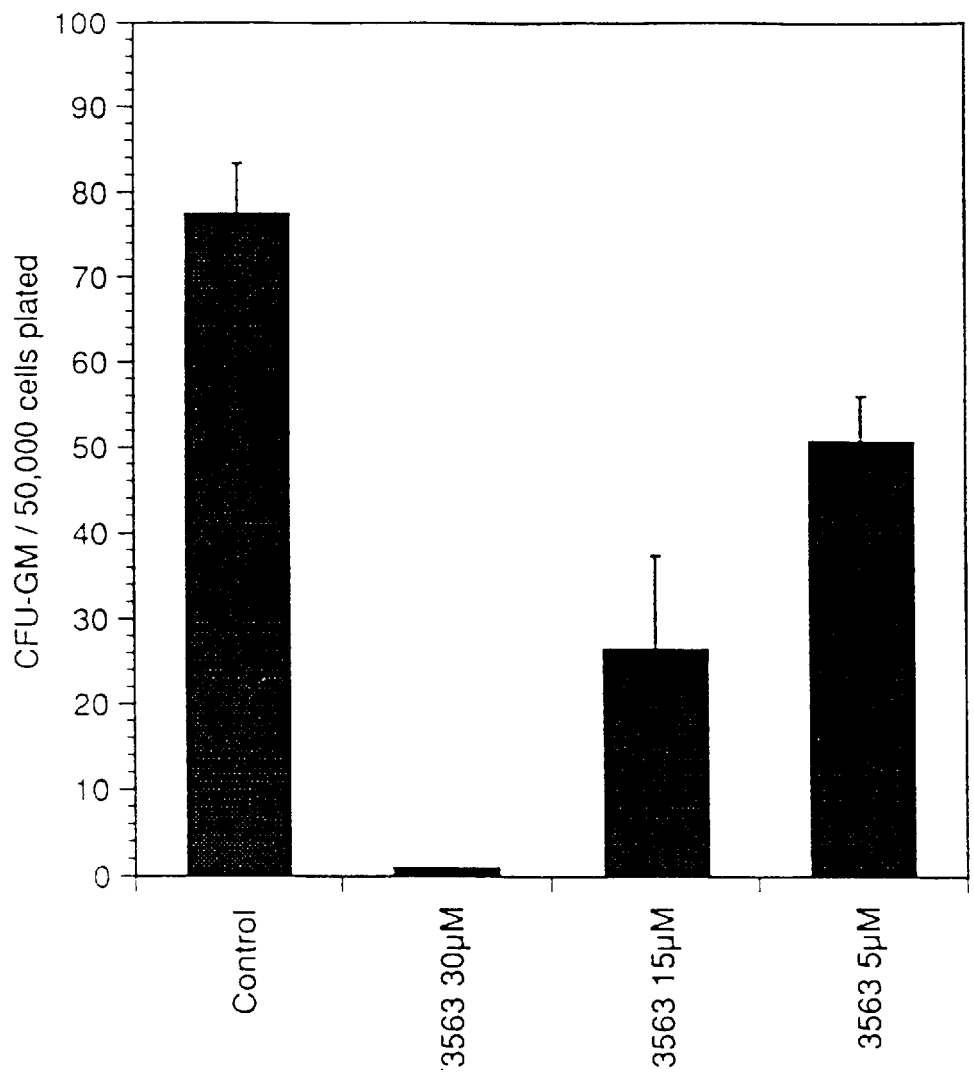
FIGS. 12, 13, 14, 15 and 16 illustrate data obtained for inventive compounds nos. 3563, 3576, 3581, 3584 and 4500, respectively, in a cancer screening assay used to evaluate whether the inventive compounds, potential cancer therapies, have cytotoxic effects on normal human bone marrow cells.
Figure 13:
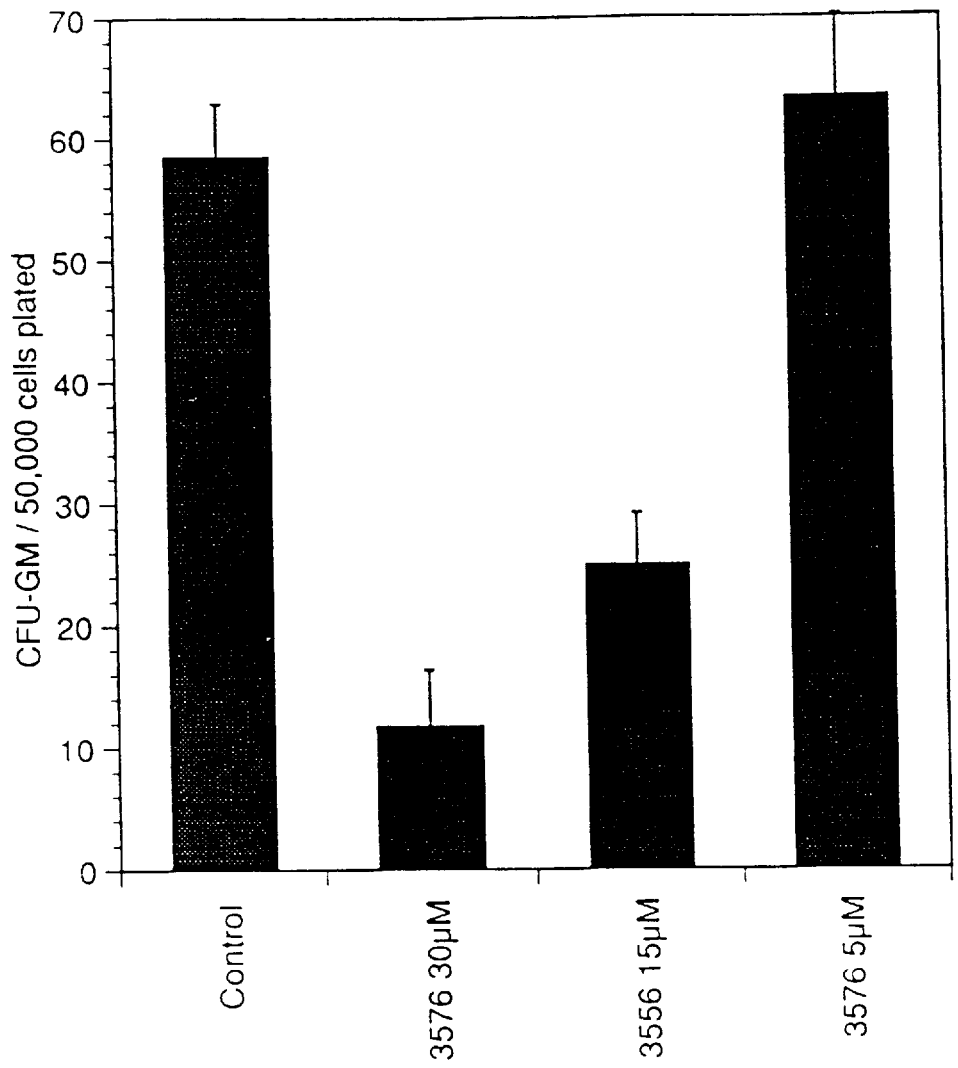
Figure 14:
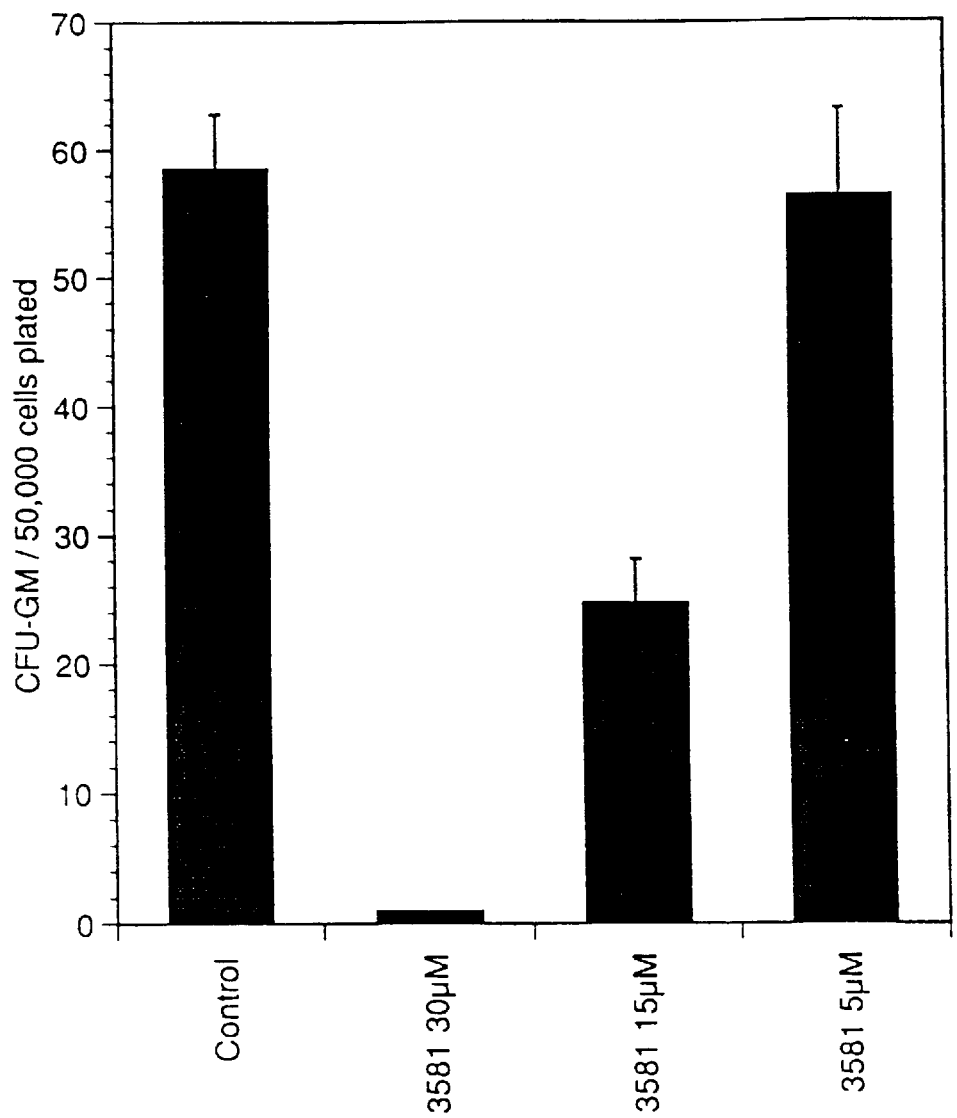
Figure 15:
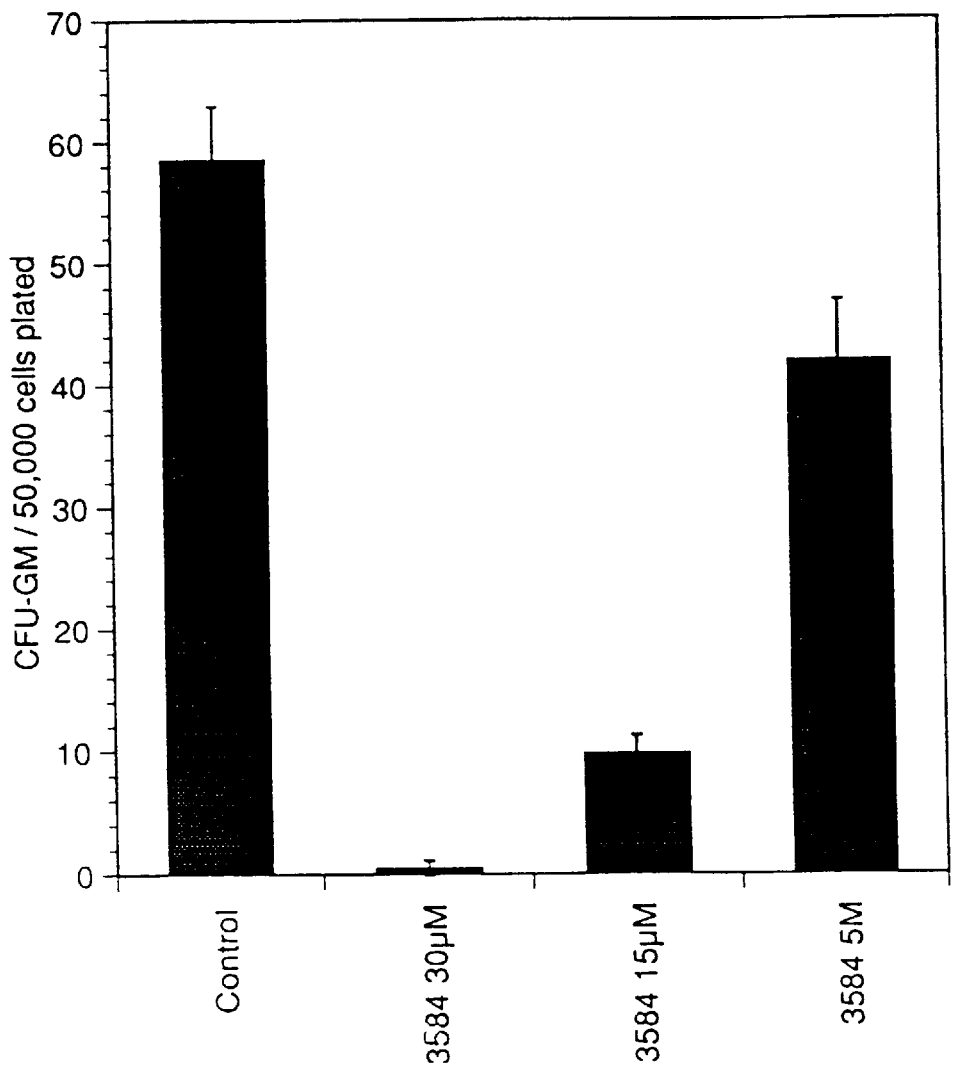

Thymuses, obtained from normal, female Balb/C mice, were dissociated and plated into 96-well plates at a density of $2\times10^5$ cells/well. Con A (0.25 mg/ml) and IL-2 (15 U/ml) were added to the wells. The cells were incubated for 4 days at 37° C. On day 4, the cells were pulsed with tritiated thymidine and incubated for an additional 4 hours. Incorporated tritiated thymidine of harvested cells was determined in a liquid scintillation counter. Results plotted as dose concentration versus proliferation for inventive compounds nos. 3506, 3556, 3563, 3576, 3581, 3582 and 3584 are shown in FIGS. 6 (3506), 7 (3556), 8 (3563), 9 (3576), 10 (3581 and 3582) and 11 (3584). Respective concentrations of inventive compound (shown in the figures) were added two hours prior to Con A and IL-2 activation. Background counts were less than 200 cpm. The inventive compounds tested inhibited thymocyte proliferation and activation at relatively low concentrations with $IC_{50}$ values ranging from 0.26 to 2.3 $\mu$M (for compounds nos. 3576 and 3506, respectively).

EXAMPLE 8

This example illustrates a method for examining an effect of the inventive compounds, showing potential as cancer therapies, on normal cells. This assay has been used clinically to evaluate recovery of patients' marrow following chemotherapy or radiation. In this specific example, inventive compounds nos. 3563, 3576, 3581 and 3584 were less deleterious to normal cells as compared to known chemotherapeutic compounds in vitro, such as, for example, vinblastine, 5-fluorouracil, doxorubicin or cisplatinum.

Mouse bone marrow cells are useful in this assay because they produce colonies, which can later be counted, in culture. The colonies are called colony forming unit-granulocyte macrophage (CFU-GM) and depend on a source of colony stimulating factor for growth.

Mouse spleen conditioned-medium, at a concentration of 2%, was used in this assay. The medium and semi-solid culture mix were procured from Stem Cell Technologies in Vancouver, BC. In animal studies performed in a related cytoreductive treatment analysis, no CFU-GM were detectable in mouse femoral marrow during immediate days following 5-fluorouracil or treatment.

Figure 16:
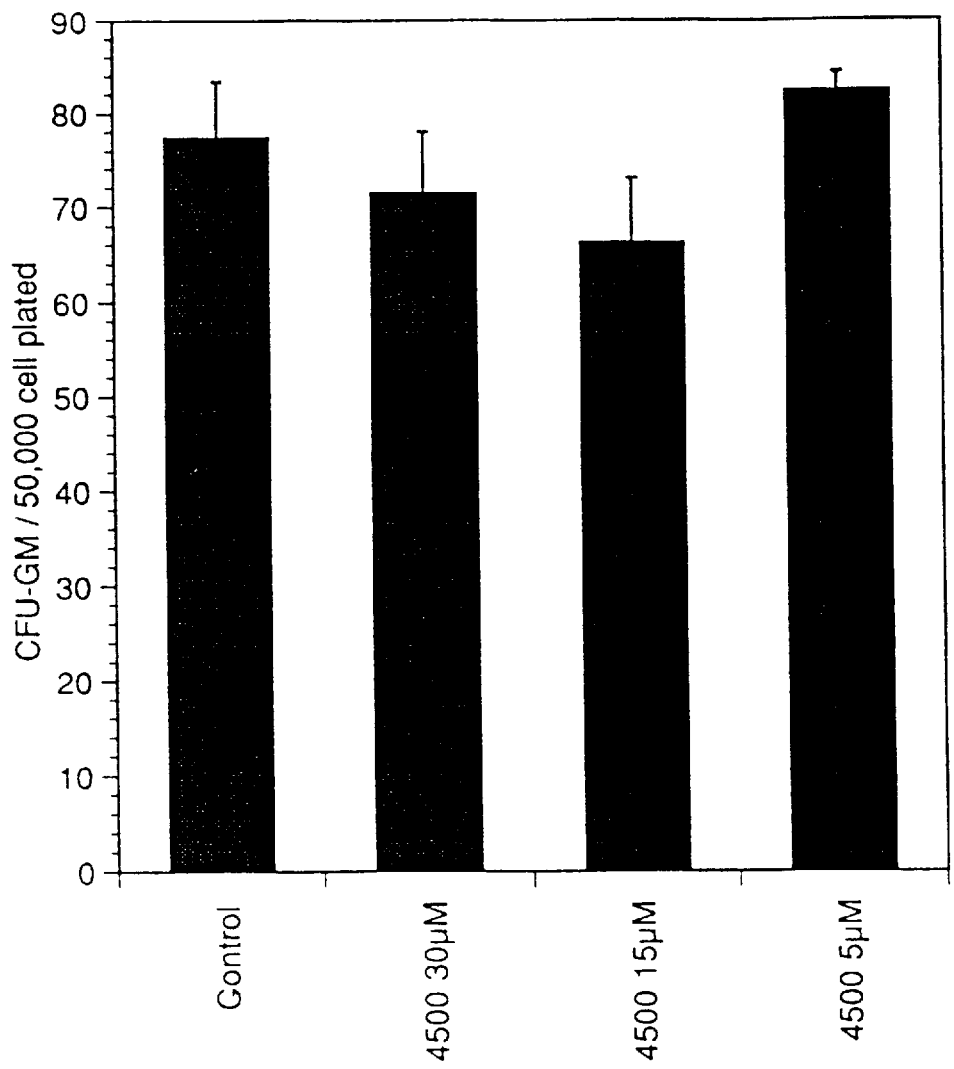

Cells were cultured with inventive compounds nos. 3563, 3576, 3581, 3584 and 4500, to comparatively evaluate an effect on normal cells of inventive compounds identified as potential cancer therapies. Procedurally, cells were incubated for 8 hours with various concentrations of these compounds. A negative control without any compound was simultaneously prepared. After 8 hours, the incubated cells were washed thoroughly and a consistent number were subsequently plated to obtain CFU-GM. Colonies were permitted to grow for 7 days at 37° C., in 5% $CO_2$. After 7 days of growth, colony growths were counted microscopically. Data obtained in this assay for inventive compounds nos. 3563, 3576, 3581, 3584 and 4500 are plotted in FIGS. 12, 13, 14, 15 and 16, respectively. The data in the figures are shown to compare the colonies counted for cells incubated with varying concentrations of the compounds tested against the negative control, without compound. At concentrations ranging from 5 to 30 $\mu$M, more colonies existed for cells incubated with the inventive potential cancer compound than with known, chemotherapeutic agents. Compound no. 3563 was the most cytotoxic to proliferative potential of the mouse marrow cells, however, compound no. 4500 showed virtually no toxicity for the normal mouse marrow cells, as shown in FIG. 16.

These compounds tested exhibit potential as anti-cancer therapeutics. They are cytotoxic to cancer tumor cells. The results from this assay were used to predict whether these inventive compounds, which have anti-cancer potential, would be toxic to normal cells, such as the bone marrow cells representative of cells known to be adversely affected by known cancer therapies. As shown in these results, the inventive compounds are generally far less cytotoxic to normal bone marrow cells than known therapies and surprisingly, compound no. 4500 has virtually no toxicity at elevated concentrations for the normal mouse marrow cells. Such potential therapies which exhibit specific toxicity to tumor cells but are not cytotoxic to normal cells predicts remarkable treatment potential for cancers.

EXAMPLE 9

This example is an assay used to measure anti-viral activity of inventive compounds nos. 3556, 3563, 3576, 3580, 3581, 3582, 3584, 3590, 3593, 4500, 4507 and 4508, by evaluating the extent to which the compounds inhibit gene expression directed by specific viral promoters in cell lines. This assay is predictive of anti-viral activity for retroviruses. Specifically, a plasmid construct, pHIV.AP, using the human immunodeficiency virus (HIV) long terminal repeat (LTR) promotor [derived from pU3R-III CAT (Sodroski et al. *Science,* Vol. 227, page 171, 1985) to direct the expression of secreted human placental alkaline phosphatase reporter gene and an expression vector for a 72 amino acids tat protein from HIV (Frankel et al., *Cell,* Vol. 55, pages 1189–1193, 91988) were transfected into a tumor cell line (e.g., 293-EBNA cells). The stably transfected cells were treated with various concentrations of the inventive compounds. The expression of the alkaline phosphatase (AP) reporter gene in the individual cultures was then measured by following the change in absorbance at A405 of cell conditioned media in the presence of a suitable substrate (e.g., ortho-nitrophenol phosphate). Berger et al., *Gene,* Vol. 66, pages 1–10, 1988.

The effect of respective inventive compounds on the viability of 293-EBNA cells was measured by a colorimetric assay that uses the alamarBlue® dye (purchased from Alamar Biosciences, Inc.) to report cell proliferation, viability and cytotoxicity. This dye is an oxidation-reduction (Redox) indicator that changes color in response to chemical reduction of growth medium resulting from cell growth. The general procedure involves adding alamar-Blue® in an amount equal to 10% of the culture volume, returning the culture to incubator for four hours, and measuring the absorbance at 570 nm after subtraction of background absorbance at 600 nm.

Figure 17:
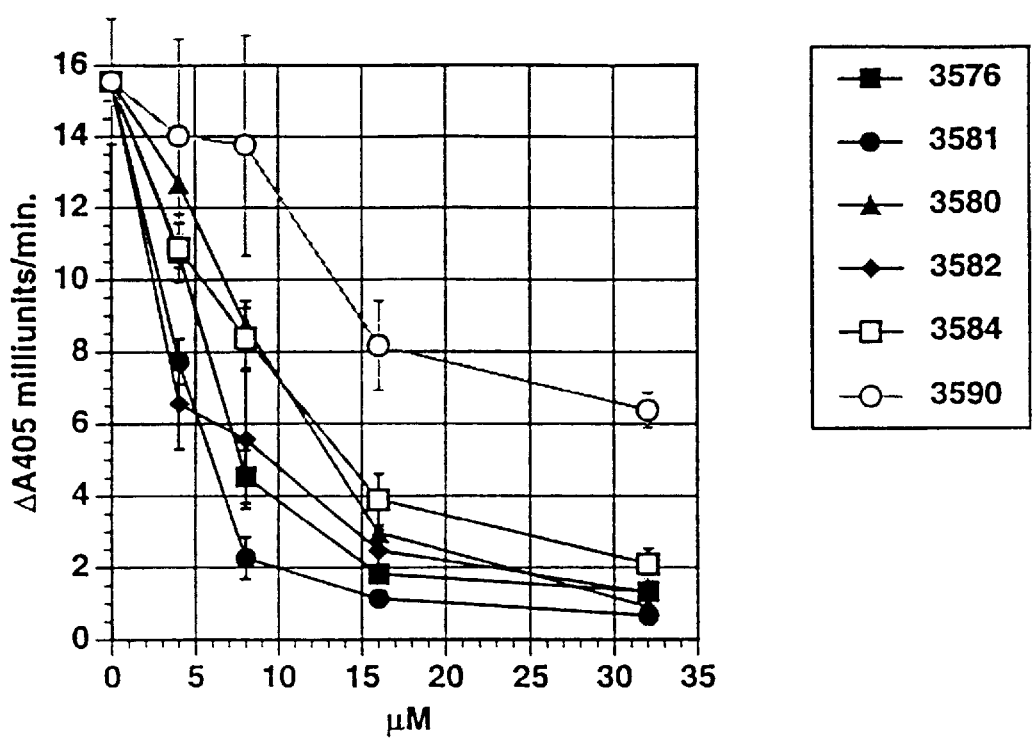
FIGS. 17, 18, 19, 20 and 21 illustrate results obtained for inventive compounds nos. 3556, 3563, 3576, 3580, 3581, 3582, 3584, 3590, 3593, 4500, 4507 and 4508 in an assay measuring anti-viral activity of the inventive compounds for inhibiting gene expression directed by specific viral promoters in cell lines.

Results obtained are shown in FIGS. 17, 18, 19, 20 and 21. FIG. 17 report data for inventive compounds nos. 3576, 3580, 3581, 3582, 3584 and 3590, showing the effect of these inventive compounds on expression of reporter gene directed by the HIV-LTR promotor in 293-EBNA cells. Compounds nos. 3581 and 3582 inhibited HIV-LTR expression by 50% ($IC_{50}$) at <5 $\mu$M; compounds nos. 3576, 3584, and 3580 at <10 $\mu$M; and compound no. 3590 at <20 $\mu$M.

Figure 18:
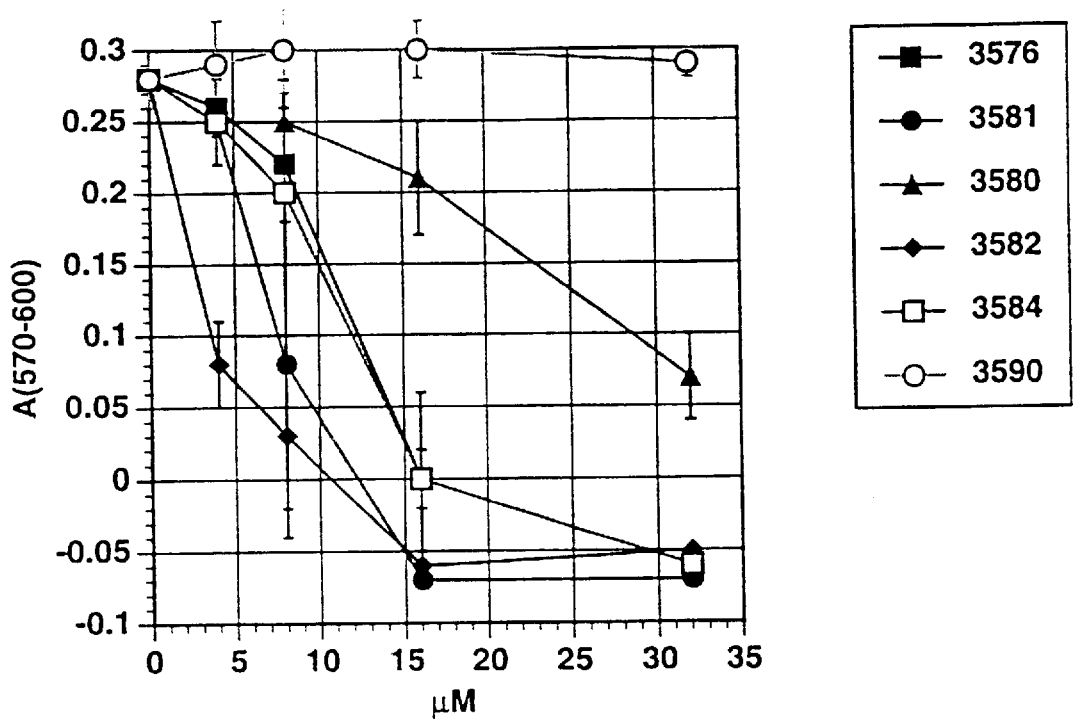

Corresponding cytotoxic effects of these compounds on 293-EBNA cells is shown in FIG. 18. Compounds nos. 3581 and 3582 had lethal dose 50% ($LD_{50}$) values for 293-EBNA cells at <10 μM and <5 μM, respectively; compounds nos. 3576 and 3584 at <15 μM; compound no. 3580 at <30 μM; and compound no. 3590 had little cytotoxicity even at >32 μM. Inventive compound no. 3580 inhibits HIV-LTR expression by 50% at <10 μM and with minimal cytotoxicity. The compounds that inhibit 293-EBNA cell viability by 50% at <10 μM show the greatest potential for use as an anti-cancer therapeutic also, as some of the inventive compounds exhibit tumor suppression activity.

Figure 19:
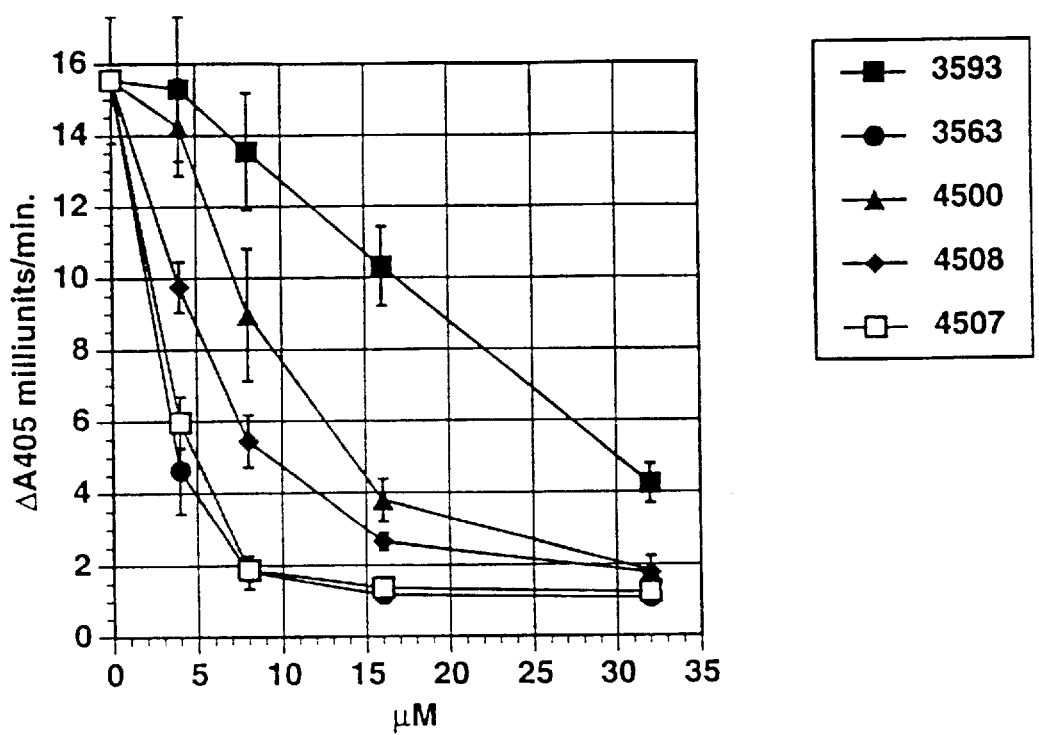
Figure 20:
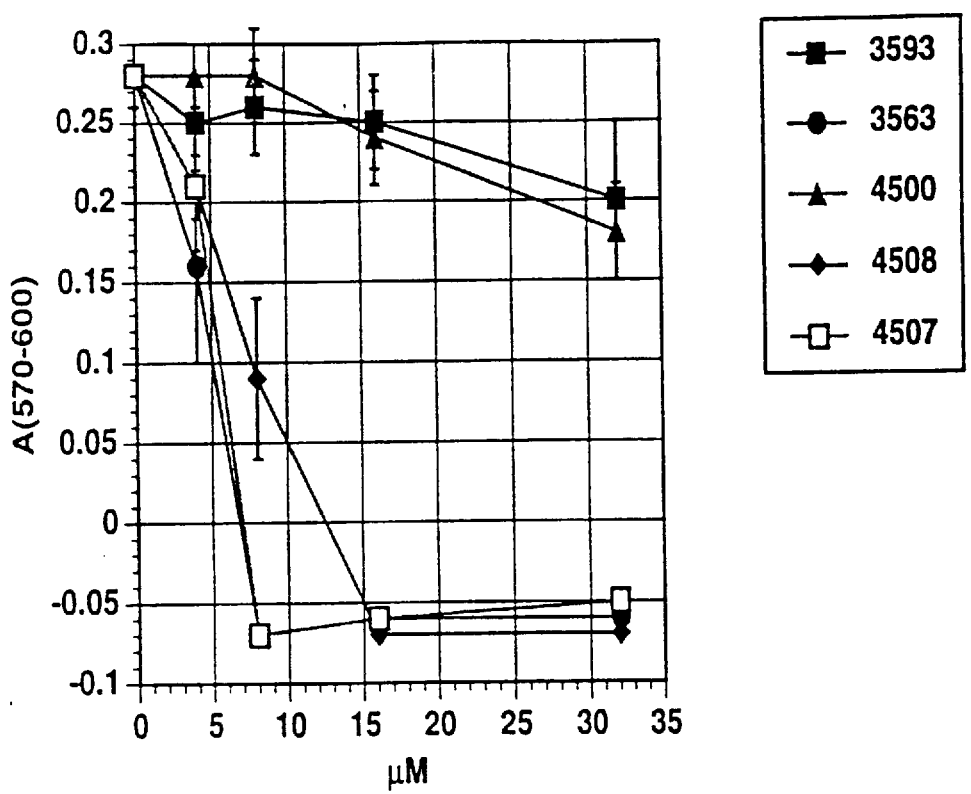

FIG. 19 shows results obtained for inventive compounds nos. 3593, 3563, 4500, 4507 and 4508 in this assay. Compounds nos. 3563 and 4507 inhibited HIV-LTR expression by 50% ($IC_{50}$) at <4 μM; compounds nos. 4508 and 4500 at <10 μM; and compound no. 3593 at <25 μM. FIG. 20 illustrates corresponding cytotoxic data of these compounds on 293-EBNA cells. Compounds nos. 3563 and 4507 have $LD_{50}$ values of <7 μM; compound no. 4508 at <10 μM; compounds nos. 3593 and 4500 have little cytotoxicity, even at >32 μM. Inventive compound no. 4500 inhibits HIV-LTR expression by 50% at <10 μM yet has minimal cytotoxic effect. The compounds that inhibit 293-EBNA cell viability by 50% at <10 μM also have the greatest potential for use as anti-cancer therapeutics.

Figure 21:
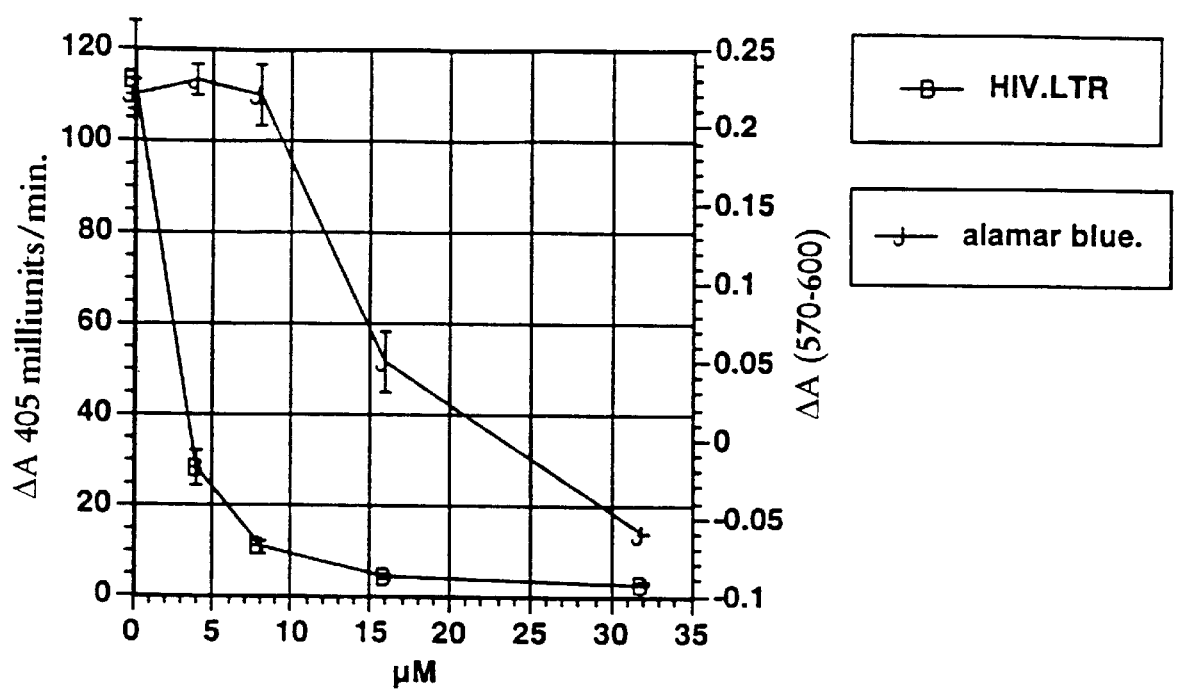

FIG. 21 illustrates results obtained in this assay for inventive compound no. 3556, having an $IC_{50}$ value of about 2.5 μM using the HIV-LTR promotor construct cotransfected with a tat expression vector. Cytotoxicity of this compound is reported as the curve corresponding to alamarBlue®. Inventive compound no. 3556 has an $LD_{50}$ value of around 12.5 μM and cytotoxicity becomes significant for this compound at concentrations >10 μM.

These assay data predict that the inventive compounds, as represented by those compounds tested, exhibit anti-viral activity, particularly against infection and viral replication of retroviruses, such as this HIV virus.

EXAMPLE 10

This example shows an ability of the inventive compounds, as represented by inventive compound no. 3556, to prevent promotion of fresh isolates of JR-CSF strain of HIV-1 infection of human peripheral blood lymphocytes (PBL).

In a protocol for infecting a PBL cell suspension, JR-CSF HIV-1 was clarified at low-speed centrifugation (2,000–3,000 rpm) or filtration and stored in aliquots at −70° C. To maintain consistent titers, HIV-1 aliquots were not subjected to repeated freezing and thawing and any remainder was discarded. Virus aliquots were thawed at room temperature or under cold running water for more rapid thawing and maintained in ice after thawing. Just prior to infection of PBL cells, the supernatant or dilution were warmed to room temperature.

Human PBL cells taken from a suitable donor were centrifuged down at 1000 rpm for 5–10 minutes at room temperature. While cells were spinning, the virus inoculum was prepared in medium by adding 10 μg/ml Polybrene®. The centrifuged cells were resuspended in virus inoculum, using 1 ml of virus inoculum per $10^7$ cells. A more efficient HIV-1 infection is obtained with smaller amounts of inoculum. The cells were incubated at 37° C. in the presence of virus inoculum for 2 hours, shaking the suspension every half hour. After 2 hours, the suspension was spun down, the virus inoculum removed and the cells were washed with 10 ml of fresh media.

The infected cells, inoculated with virus at a concentration of 10 ng virus/$10^6$ PBL, were washed and resuspended in growth medium (serum-free RPMI/20 % FBS/10 units/ml IL-2). The washed and resuspended cells were added to each well of a 24-well plate at a concentration of approximately $10^6$ cells/well. The respective inventive compound was added to the wells at various concentrations, in triplicate. Supernatant from respective wells was harvested after days four and seven, 1 ml of fresh growth medium with antiretroviral agent was added and the samples collected were stored at −70° C. On day fourteen, a final supernatant was harvested and p24 antigen ELISA analysis was performed on respective supernatant samples collected to determine whether the inventive compounds prevented viral infection.

Figure 22:
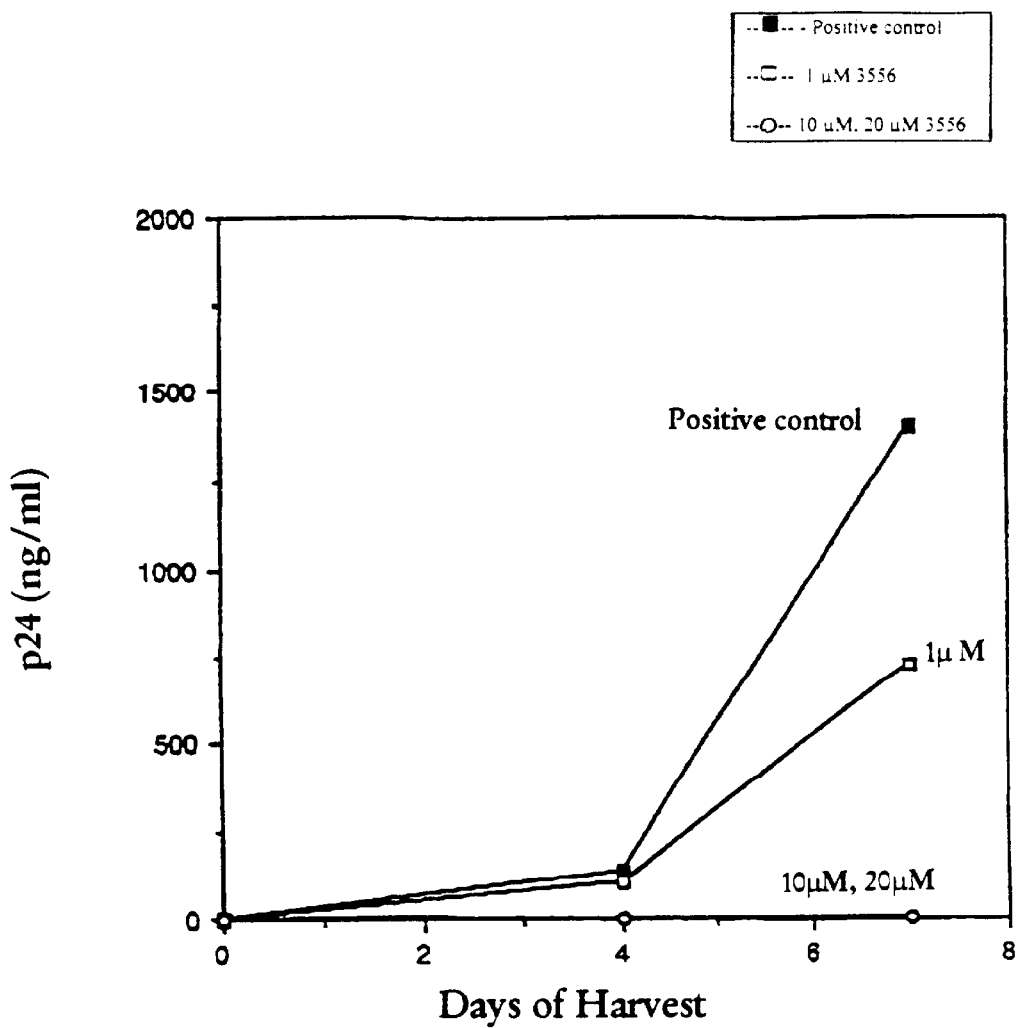
FIG. 22 illustrates an ability of the inventive compounds, as represented by inventive compound no. 3556, to prevent promotion of JR-CSF strain of HIV-1 infection of human peripheral blood lymphocytes (PBL).

The analysis results are graphically represented in FIG. 22 for inventive compound no. 3556. Inventive compound no. 3556 exhibited even more remarkable results in preventing infection. As shown in FIG. 22, at 1 μM, compound no. 3556 decreased infection by about two to three fold, but at 10 and 20 μM concentrations, compound no. 3556 virtually eliminated viral infection by this HIV-1 strain. At 20 μM concentrations, some cell death began to occur at day seven. These results confirm that the inventive compounds, as represented by the tested specie, predict potent anti-viral activity against HIV and are thus effective therapeutics as anti-viral agents (particularly retroviruses) and for treating AIDS and AIDS-related indications.

Comparative Example 1

Figure 23:
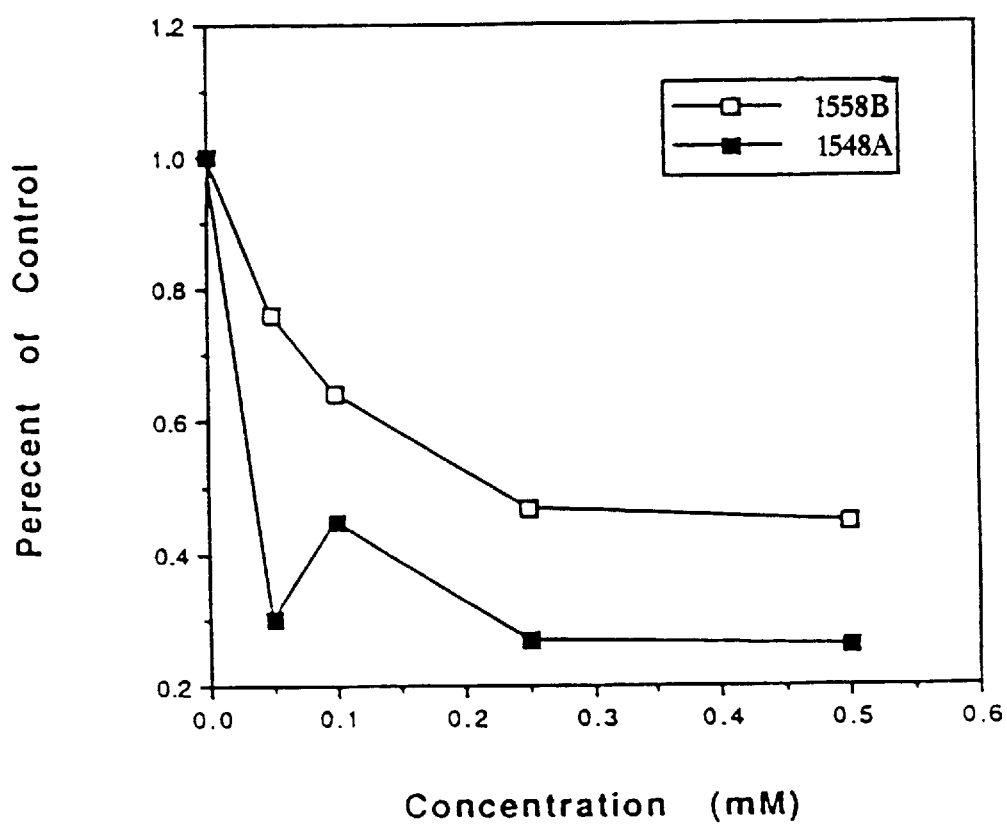
FIG. 23 shows the effects of two comparative compounds on PDGF-induced proliferation in human stromal cells.

This example illustrates the effects of comparative compounds A and B [1-(7-oxooctyl)-3,7-dimethylxanthine and 1-(5-dimethylaminohexyl)-3,7-dimethylxanthine, respectively] on inhibition of PDGF-induced proliferation in human stromal cells. Human stromal cells were starved in serum-free media for 24 hours and then stimulated with 50 ng/ml PDGF-BB. The drugs were added at various concentrations one hour prior to PDGF stimulation. Tritiated thymidine was added at the time of PDGF stimulation and pulsed for 24 hours. Cells were harvested and cell proliferation measured (FIG. 23). Background counts (i.e., starved cells) were about 10% of control levels.

When compared with results obtained for the inventive compounds in a related assay using Balb/3T3 cells in place of human stromal cells (as shown in Example 5), these comparative compounds do not exhibit the significant therapeutic potential of the inventive compounds. The inventive compounds differ structurally from comparative compounds A and B at the amine substituents. The activity of the comparative compounds is apparent in millimolar concentrations, whereas the inventive compounds exhibit far more substantial activity in the micromolar range. Surprisingly, the inventive compounds have remarkably increased therapeutic potential over these comparative compounds.

What is claimed is:

1. A method for treating a disease caused by an undesirable cell response that is mediated by a proliferative intracellular signaling pathway, the method comprising administering an effective amount of a compound, resolved enantiomers, diastereomers, hydrates, salts, solvates and mixtures thereof, the compound having the formula $$\text{CORE MOIETY}-(R)_j$$

wherein:

j is an integer from one to three;

the core moiety is xanthinyl; and

R is independently seleced from the group consisting of amine, hydrogen, halogen, hydroxyl, $C_{(1-10)}$ alkyl, $C_{(2-10)}$ alkenyl, 2-bromopropyl, 4-chloropentyl, cyclohexyl, cyclopentyl, 3-dimethylaminobutyl, 2-hydroxyethyl, 5-hydroxyhexyl, 3-hydroxy-n-3-hydroxypropyl, 2-methoxyethyl, 4-methoxy-n-butyl, phenyl, and formula I, at least one R comprising formula;

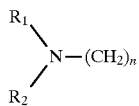

wherein;

($CH_2$) is optionally substituted;

n is an integer from five to twenty;

each $R_1$ or $R_2$ is independently hydrogen, optionally substituted $C_{(1-20)}$ alkyl, $C_{1-20)}$ alkoxyl, $C_{(2-20)}$ alkenyl, or an optionally substituted carbocyclic or heterocyclic ring selected from the group consisting of anthracenyl, bicyclo[4.4.0]decanyl, bicyclo[2.2.1]heptanyl, bicyclo[4.1.0]heptanyl, bicyclo[2.2.1]hexanyl, bicyclo[4.3.0]nonanyl, bicyclo[2.2.2]octanyl, biphenyl, cyclopentadienyl, cyclopentanyl, cyclobutanyl, cyclobutenyl, cycloheptanyl, cyclohexanyl, cyclooctanyl and cyclopropanyl, 1,2-diphenylethanyl, fluorenyl, indenyl, phenyl, quinonyl, terphenyl, naphthalenyl, phenanthrenyl terphenyl, toluene, xylenyl, azetidinyl, benzofuranyl, carbazolyl, furanyl, glutarimidyl, indolyl, isoquinolinyl, oxatanyl, oxiranyl, phthalimidyl, piperidinyl, pyrrolidinyl, pyranyl, pyridinyl, pyrrolyl, quinolinyl, tetrahydrofuranyl, tetrahydropyranyl, tetrahydrothiophenyl, thiophenyl and thyminyl, with the proviso that at least one of $R_1$ or $R_2$ is other than hydrogen or methyl; and wherein, when the $CH_{(2)n}$, $R_1$ or $R_2$ is substituted, the substituent is selected from the group consisting of carbamoyl, primary, secondary and tertiary amino $C_{(2-8)}$ alkenyl, $C_{(1-8)}$ alkyl, $C_{(1-8)}$ alkoxyl, $C_{(1-8)}$ hydroxyalkyl,, azido, carbonato, carbonyl, carboxyl, cyano, $C_{(1-8)}$ haloalkyl, isocyano, isomercaptocyano, phospho, phosphonato, sulfonato, alkylsulfonyl, alkylsuloxidyl, mercaptocarbonyl, mercaptocarbonato, thioureido and ureido.

2. The method of claim 1, wherein n is an integer from five to sixteen.

3. The method of claim 1, wherein n is an integer from seven to fourteen.

4. The method of claim 1, wherein the xanthinyl is selected from the group consisting of 3-methylxanthinyl and 3,7-dimethylxanthinyl.

5. The method of claim 1 wherein R is bonded to a nitrogen of the core moiety with the proviso that when R is a halogen, then R is not bound to a nitrogen atom.

6. The method of claim 1 wherein said undesirable cell response is PDGF-induced proliferation.

7. The method of claim 1, wherein said undesirable cell response is JR-CSF HIV-1 infection.

8. The method of claim 1, wherein said undesirable cell response is gene expression directed by HIV LTR promoter.

9. The method of claim 1, wherein the proliferative intracellular signaling pathway is a second messenger pathway.

10. The method of claim 1, wherein said disease is a member selected from the group consisting of acute or chronic inflammatory disease, AIDS and AIDS related complex, angiogenesis, atherosclerosis, myelogenous leukemia, coronary artery disease, fibrosis, glomerular nephritis, lupus, restenosis, rheumatoid arthritis, scleroderma, and transplant rejection.

11. The method of claim 1, wherein said disease is an autoimmune disease.

12. The method of claim 1, wherein said disease is multiple sclerosis.

13. A method for treating a disease caused by an undesirable cell response that is mediated by a proliferative intracellular signaling pathway, the method comprising administering an effective amount of a compound selected from the group consisting of:

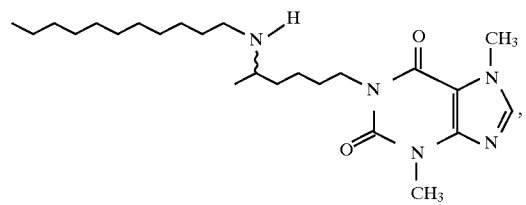

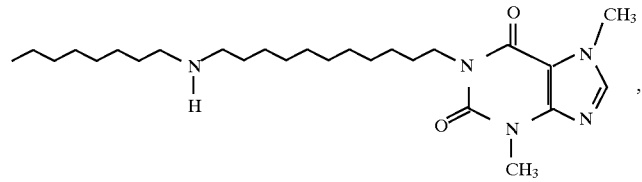

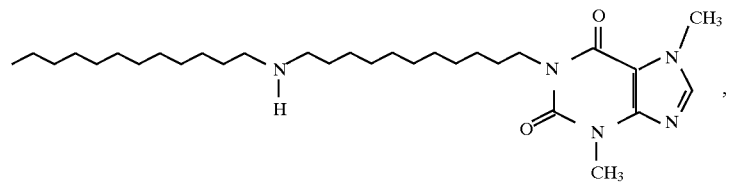

-continued
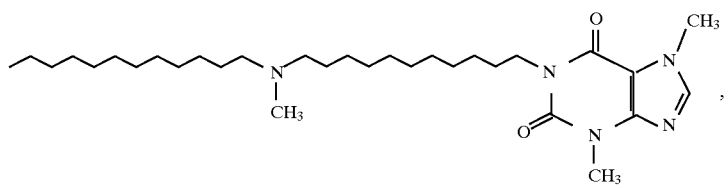
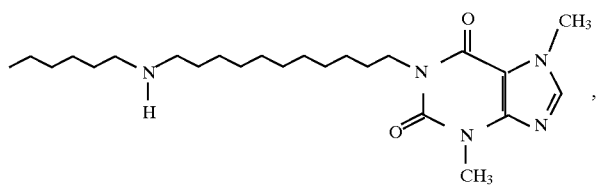
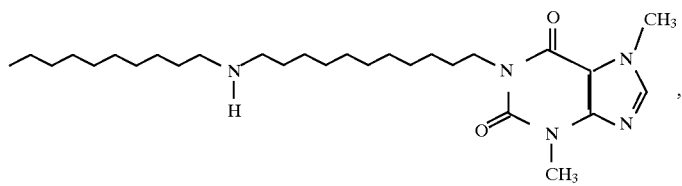
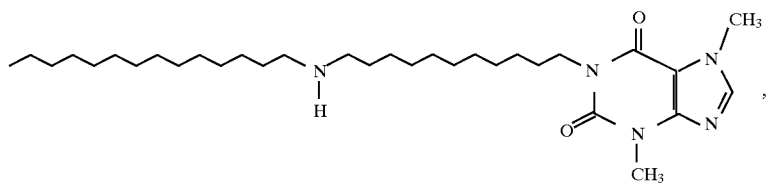
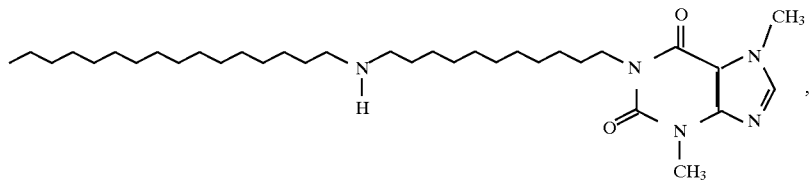
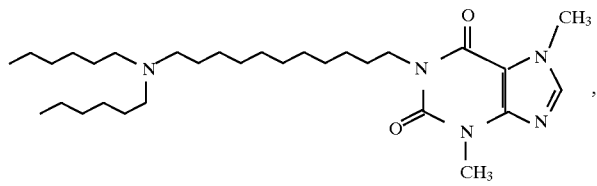
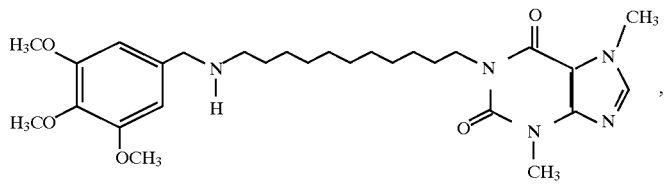
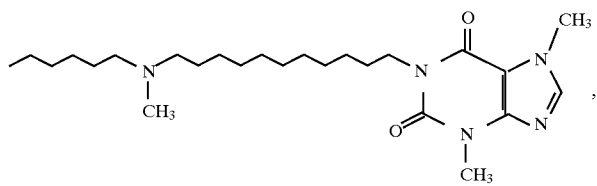

-continued
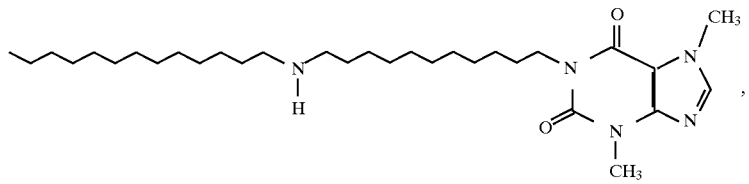
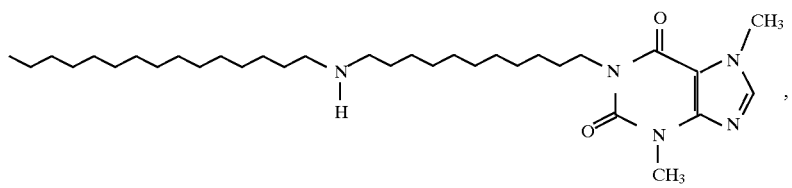
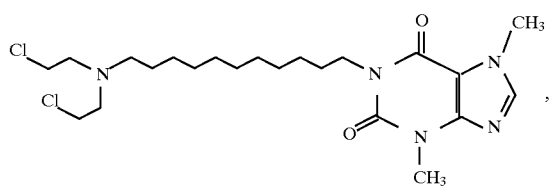
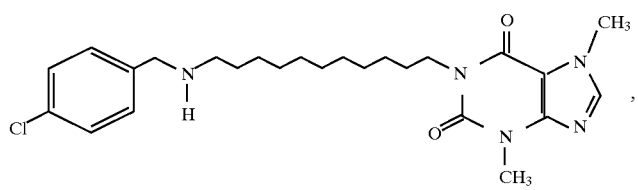
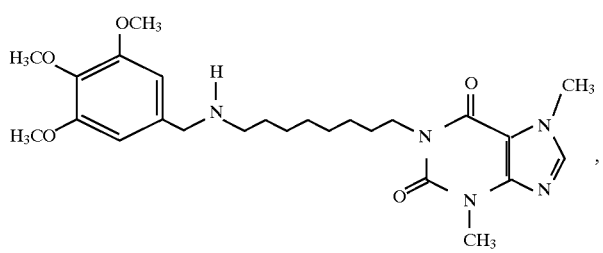
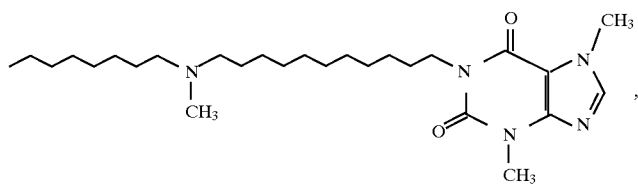
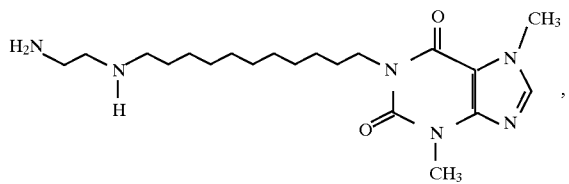
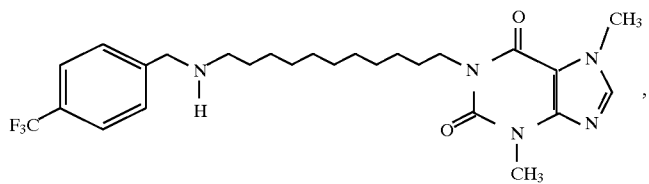

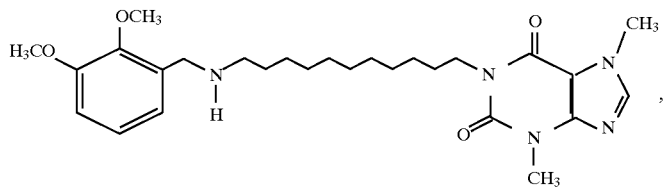,
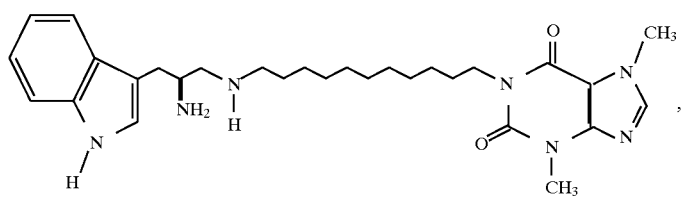,
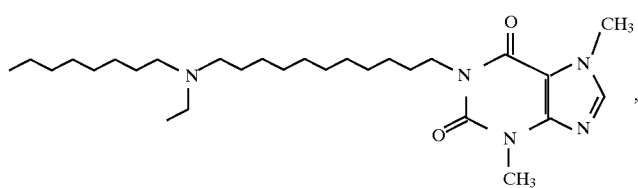,
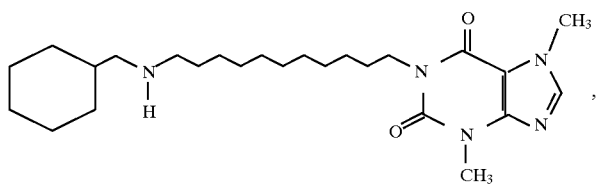,
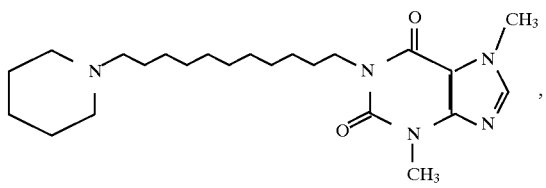,
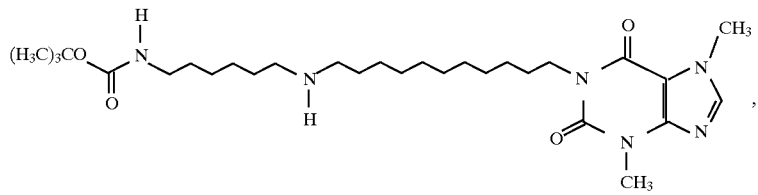,
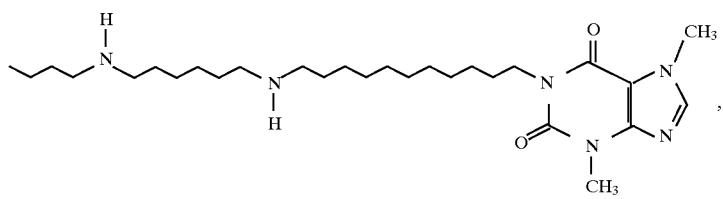,
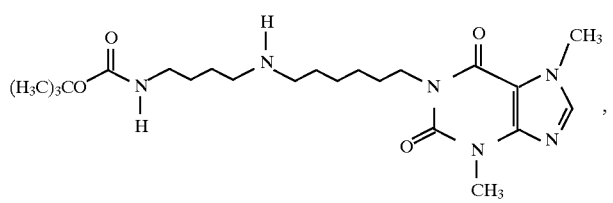, -continued
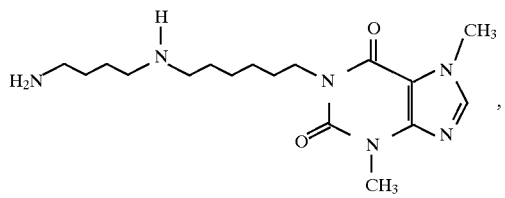,
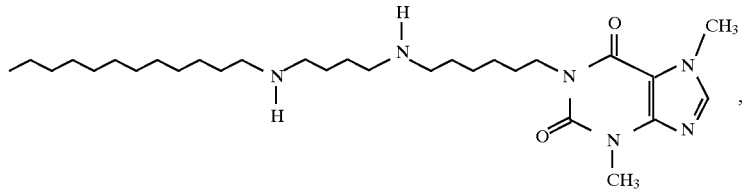,
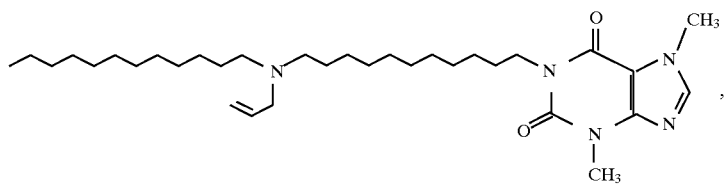,
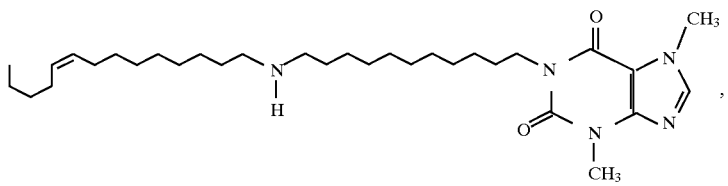,
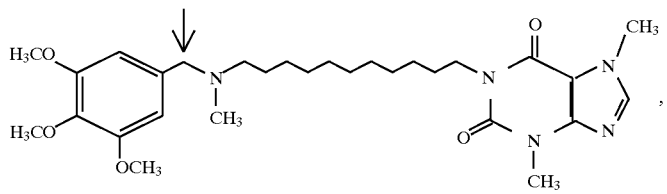,
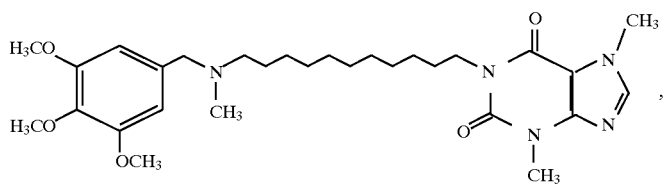,
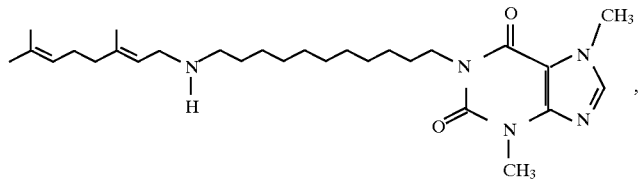,
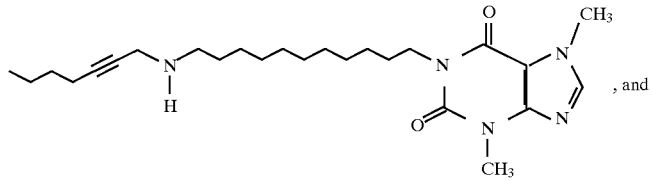, and -continued

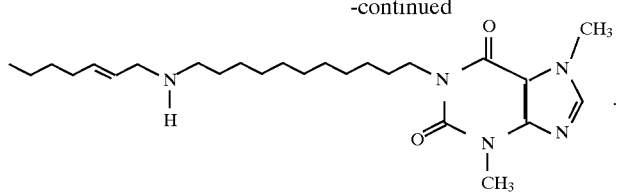

14. A method for treating a disease caused by an undesirable cell response that is mediated by a proliferative intracellular signaling pathway, the method comprising administering an effective amount of a compound, resolved enantiomers, diastereomers, hydrates, salts, solvates or mixtures thereof, the compound being selected from the group consisting of

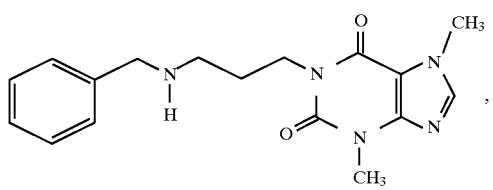

,

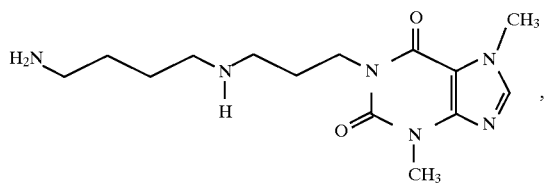

,

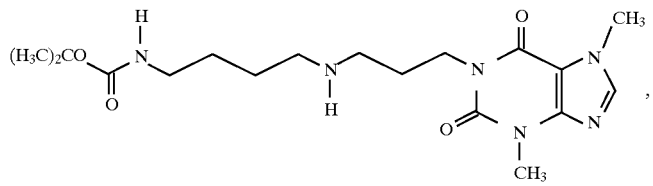

,

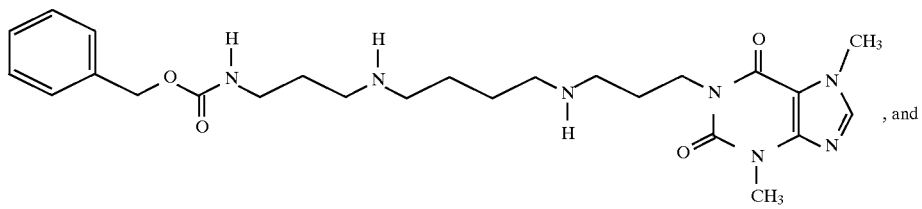

, and

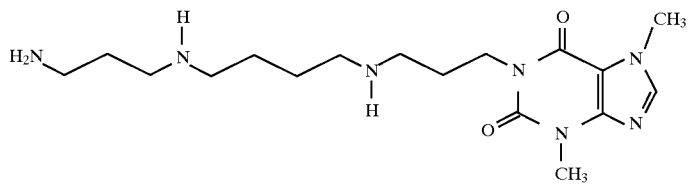

15. The method of claim 14, wherein said undesirable cell response is PDGF-induced proliferation.

16. The method of claim 14, wherein said undesirable cell response is JR-CSF HIV-1 infection.

17. The method of claim 14, wherein said undesirable cell response is gene expression directed by HIV LTR promoter.

18. The method of claim 14, wherein the proliferative signaling pathway is a second messenger pathway.

19. The method of claim 14, wherein said disease is a member selected from the group consisting of acute or chronic inflammatory disease, AIDS and AIDS related complex, angiogenesis, atherosclerosis, myelogenous leukemia, coronary artery disease, fibrosis, glomerular nephritis, lupus, restenosis, rheumatoid arthritis, scleroderma and transplant rejection.

20. The method of claim 14, wherein said disease is an autoimmune disease.

21. The method of claim 14, wherein said disease is multiple sclerosis.

* * * * *

UNITED STATES PATENT AND TRADEMARK OFFICE
CERTIFICATE OF CORRECTION

PATENT NO. : 5,807,861
DATED : September 15, 1998
INVENTOR(S) : KLEIN et al.

It is certified that error appears in the above-identified patent and that said Letters Patent is hereby corrected as shown below:

Claim 1

Col. 43, line 6 change "3-hydroxy-n-3-hydroxypropyl" to --3-hydroxy-n-butyl, 3-hydroxypropyl--.

Col. 43, line 9 after "formula" insert --I--.

Col. 43, line 16 change "$(CH_2)$" to --$(CH_2)_n$--.

Col. 43, line 20 change "(C1-20)" to --$C_{(1-20)}$--.

Col. 43, line 24 after first occurrence "heptanyl" insert --bicyclo[3.2.0]heptanyl--.

Col. 43, line 30 change "toluene" to --toluenyl--.

Col. 43, line 30 after "benzofuranyl," insert --benzothiophenyl--.

Col. 43, line 32 delete "oxatanyl" and insert --oxazolyl, oxetanyl--.

Col. 44, line 1 delete ",," and insert --,--.

Col. 44, line 4 delete "alkylsuloxidyl" and insert --alkylsulfoxidyl--.

Claim 13

Col. 49, line 3 insert

-- 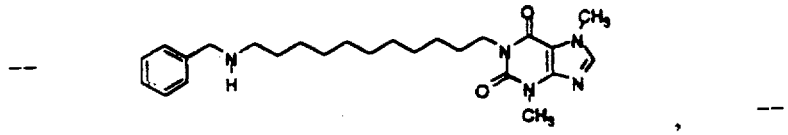 , --

UNITED STATES PATENT AND TRADEMARK OFFICE
CERTIFICATE OF CORRECTION

PATENT NO. : 5,807,861
DATED : September 15, 1998
INVENTOR(S) : KLEIN et al.

It is certified that error appears in the above-identified patent and that said Letters Patent is hereby corrected as shown below:

Col. 49, line 7 insert

-- 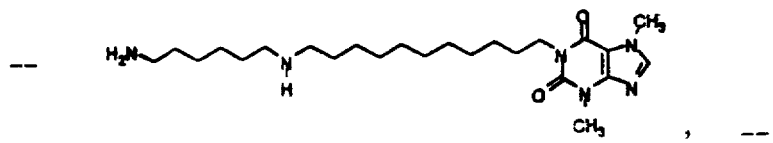 , --

Signed and Sealed this

Fourth Day of May, 1999

Attest:

Attesting Officer

Q. TODD DICKINSON

Acting Commissioner of Patents and Trademarks